(12) United States Patent
Hwang et al.

(10) Patent No.: US 10,517,910 B2
(45) Date of Patent: Dec. 31, 2019

(54) COMPOSITIONS AND METHODS FOR VIRAL EMBOLIZATION

(71) Applicant: SillaJen, Inc., Busan (KR)

(72) Inventors: Tae Ho Hwang, Busan (KR); Nam Hee Lee, Busan (KR); Mong Cho, Busan (KR); Ungbae Jeon, Busan (KR); Doo Jin Byun, Daejeon (KR)

(73) Assignee: SILLAJEN, INC., Busan (KR)

( * ) Notice: Subject to any disclaimer, the term of this patent is extended or adjusted under 35 U.S.C. 154(b) by 0 days.

(21) Appl. No.: 15/738,034

(22) PCT Filed: Jun. 17, 2016

(86) PCT No.: PCT/IB2016/000993
§ 371 (c)(1),
(2) Date: Dec. 19, 2017

(87) PCT Pub. No.: WO2017/037523
PCT Pub. Date: Mar. 9, 2017

(65) Prior Publication Data
US 2018/0303886 A1 Oct. 25, 2018

Related U.S. Application Data

(60) Provisional application No. 62/182,383, filed on Jun. 19, 2015.

(51) Int. Cl.
*A61K 35/768* (2015.01)
*C12N 7/00* (2006.01)
*A61K 9/00* (2006.01)
*A61K 47/42* (2017.01)
*A61K 38/19* (2006.01)
*A61K 35/763* (2015.01)
*A61P 35/00* (2006.01)

(52) U.S. Cl.
CPC .......... *A61K 35/768* (2013.01); *A61K 9/0024* (2013.01); *A61K 35/763* (2013.01); *A61K 38/193* (2013.01); *A61K 47/42* (2013.01); *A61P 35/00* (2018.01); *C12N 7/00* (2013.01); *C12N 2710/24132* (2013.01); *C12N 2710/24171* (2013.01)

(58) Field of Classification Search
CPC .... A61K 2300/00; A61K 9/0019; A61K 9/06; A61K 38/00; A61K 39/39; A61K 9/0024; A61K 39/12; A61K 9/127; A61K 8/042; A61K 9/1271; A61K 2039/55555; A61K 9/1075; A61K 9/1273; A61K 9/1277; A61K 35/76; A61K 48/0075; A61K 8/0216; A61K 8/068; A61K 8/14; A61K 9/51; A61K 35/768; A61K 35/763; A61K 38/193; A61K 47/42; A61L 27/52; A61L 15/44; A61L 27/54; A61L 31/145; A61L 2300/624; A61L 2300/626; A61L 2400/06; A61L 29/145; A61P 35/00; C12N 7/00; C12N 2710/24171; C12N 2710/24132
See application file for complete search history.

(56) References Cited

U.S. PATENT DOCUMENTS

| | | | |
|---|---|---|---|
| 5,073,627 A | 12/1991 | Curtis et al. | |
| 5,578,448 A | 11/1996 | Rota et al. | |
| 8,697,137 B2 * | 4/2014 | Vogel | A61K 9/1635 424/501 |
| 8,980,246 B2 * | 3/2015 | Kirn | A61K 38/193 424/93.2 |
| 8,986,674 B2 * | 3/2015 | Kirn | A61K 45/06 424/93.3 |
| 9,180,149 B2 * | 11/2015 | Kirn | A01K 67/0271 |
| 9,180,151 B2 * | 11/2015 | Kirn | A61K 31/4412 |
| 9,226,977 B2 * | 1/2016 | Kirn | A61K 38/193 |
| 9,719,105 B2 * | 8/2017 | Kirn | A61K 35/76 |
| 9,827,278 B2 * | 11/2017 | Kirn | A01K 67/0271 |
| 9,919,047 B2 * | 3/2018 | Kirn | A61K 39/0011 |
| 9,919,062 B2 * | 3/2018 | Kirn | A61K 38/193 |
| 2002/0098203 A1 * | 7/2002 | Gustavsson | A61K 9/1623 424/234.1 |
| 2003/0211165 A1 | 11/2003 | Vogel et al. | |
| 2004/0091458 A1 | 5/2004 | Morris et al. | |

(Continued)

FOREIGN PATENT DOCUMENTS

| | | |
|---|---|---|
| EP | 3310383 A1 | 4/2018 |
| WO | 1999/012577 A1 | 3/1999 |

(Continued)

OTHER PUBLICATIONS

Shiba H, Okamoto T, Futagawa Y, Misawa T, Yanaga K, Ohashi T, Eto Y. Adenovirus vector-mediated gene transfer using degradable starch microspheres for hepatocellular carcinoma in rats. J Surg Res. Jun. 15, 2006;133(2):193-6.*

Altomonte J, Braren R, Schulz S, Marozin S, Rummeny EJ, Schmid RM, Ebert O. Synergistic antitumor effects of transarterial viroembolization for multifocal hepatocellular carcinoma in rats. Hepatology. Dec. 2008;48(6):1864-73.*

Hastie E, Grdzelishvili VZ. Vesicular stomatitis virus as a flexible platform for oncolytic virotherapy against cancer. J Gen Virol. Dec. 2012;93(Pt 12):2529-45. doi: 10.1099/vir.0.046672-0. Epub Oct. 10, 2012.*

(Continued)

*Primary Examiner* — Rachel B Gill

(74) *Attorney, Agent, or Firm* — Polsinelli PC; Christopher M. Cabral

(57) ABSTRACT

The present disclosure relates to oncolytic viruses for use transcatheter arterial viroembolization methods. The present disclosure also provides composition with such oncolytic viruses in combination with a biocompatible microparticle or hydrophilic polymer gel agent suitable for active embolization. The present disclosure further provides methods of transcatheter arterial viroembolization using such oncolytic viruses and compositions preferably in a manner that debulks tumor.

17 Claims, 5 Drawing Sheets

Specification includes a Sequence Listing.

(56) References Cited

U.S. PATENT DOCUMENTS

| | | | | |
|---|---|---|---|---|
| 2010/0119572 | A1* | 5/2010 | Boschetti | A61K 9/1635 424/422 |
| 2010/0136092 | A1* | 6/2010 | Nakagawa | A61K 9/7053 424/449 |
| 2013/0324548 | A1* | 12/2013 | Denys | A61K 9/0019 514/252.18 |
| 2014/0086976 | A1* | 3/2014 | Szalay | C12N 7/00 424/445 |
| 2014/0194370 | A1* | 7/2014 | Cappello | A61K 38/39 514/21.2 |
| 2015/0037355 | A1* | 2/2015 | Kirn | A61K 39/0011 424/174.1 |
| 2015/0202325 | A1* | 7/2015 | Kirn | A61K 38/193 514/44 R |
| 2016/0038548 | A1* | 2/2016 | Kirn | A01K 67/0271 424/93.2 |
| 2016/0129135 | A1* | 5/2016 | Kirn | A61K 38/193 514/44 R |
| 2017/0298324 | A1* | 10/2017 | Kirn | A61K 35/76 |
| 2018/0214538 | A1* | 8/2018 | Kirn | A61K 39/0011 |
| 2018/0256751 | A1* | 9/2018 | Kirn | A61K 38/193 |

FOREIGN PATENT DOCUMENTS

| | | |
|---|---|---|
| WO | 2004/014314 A2 | 2/2004 |
| WO | 2013/022764 A1 | 2/2013 |
| WO | 2017/037523 A1 | 3/2017 |

OTHER PUBLICATIONS

Shen A, Liu S, Yu W, Deng H, Li Q. p53 gene therapy-based transarterial chemoembolization for unresectable hepatocellular carcinoma: A prospective cohort study. J Gastroenterol Hepatol. Nov. 2015;30(11):1651-6.*

Wu PZ, Zhou J, Zhang YW. Gelatin sponge microparticles for the treatment of the spontaneous rupture of hepatocellular carcinoma hemorrhage. Exp Ther Med. Oct. 2016;12(4):2201-2207. Epub Aug. 4, 2016.*

Lubarsky M, Ray C, Funaki B. Embolization agents—which one should be used when? Part 2: small-vessel embolization. Semin Intervent Radiol. Mar. 2010;27(1):99-104.*

Lubarsky M, et.al. Embolization agents—which one should be used when? Part 1: large-vessel embolization. Semin Intervent Radiol. Dec. 2009;26(4):352-7.*

Howells A, Marelli G, Lemoine NR, Wang Y. Oncolytic Viruses-Interaction of Virus and Tumor Cells in the Battle to Eliminate Cancer. Front Oncol. Sep. 8, 2017;7:195. doi: 10.3389/fonc.2017.00195. eCollection 2017.*

Aref S, Bailey K, Fielding A. Measles to the Rescue: A Review of Oncolytic Measles Virus. Viruses. Oct. 22, 2016;8(10). pii: E294.*

Bailer SM, Funk C, Riedl A, Ruzsics Z. Herpesviral vectors and their application in oncolytic therapy, vaccination, and gene transfer. Virus Genes. Oct. 2017;53(5):741-748. Epub Jun. 20, 2017.*

"Biocompatibility". Merriam-Webster Online Dictionary. Accessed Feb. 8, 2019.*

"Microparticle". Merriam-Webster Online Dictionary. Accessed Feb. 8, 2019.*

"Microparticle". Wikipedia. Accessed Feb. 8, 2019.*

Weng L, Donelson R. "Resorable Embolics". In Encyclopedia of Polymer Applications, vol. III, p. 2240, Mishra M, ed. 2019.*

Adler, Stuart P., "Human CMV Vaccine Trials: What if CMV Caused a Rash?", Journal of Clinical Virology, vol. 41, 2008, pp. 231-236.

Arvin et al., "Vaccine Development to Prevent Cytomegalovirus Disease: Report from the National Vaccine Advisory Committee", Clinical Infectious Diseases, vol. 39, 2004, pp. 233-239.

Basak et al., "Polarized Entry of Canine Parvovirus in an Epithelial Cell Line", Journal of Virology, vol. 63, No. 7, Jul. 1989, pp. 3164-3167.

Bruix et al., "Chemoembolization for Hepatocellular Carcinoma", Gastroenterology, vol. 127, No. 5, Nov. 2004, pp. S179-S188.

Cameron et al., "The Complete DNA Sequence of Myxoma Virus", Virology, vol. 264, 1999, pp. 298-318.

Camma et al., "Transarterial Chemoembolization for Unresectable Hepatocellular Carcinoma: Meta-Analysis of Randomized Controlled Trials", Radiology, vol. 224, 2002, pp. 47-54.

Chang et al., "Comparison Between Transauricular and Transfemoral Arterial Access for Hepatic Artery Angiography in a Rabbit Model", Journal of Vascular and Interventional Radiology, vol. No. 22, 2011, pp. 1181-1187.

Chang et al., "Oncolytic Virotherapy for Advanced Liver Tumours", Journal of Cellular and Molecular Medicine, vol. 13, No. 7, 2009, pp. 1238-1247.

Cui et al., "Cytomegalovirus Vaccines Fail to Induce Epithelial Entry Neutralizing Antibodies Comparable to Natural Infection", Vaccine, vol. 26, No. 45, Oct. 23, 2008, pp. 5760-5766.

Dargan et al., "Sequential Mutations Associated with Adaptation of Human Cytomegalovirus to Growth in Cell Culture", Journal of General Virology, vol. 91, 2010, pp. 1535-1546.

Elek et al., "Development of a Vaccine Against Mental Retardation Caused by Cytomegalovirus Infection in Utero", The Lancet, Jan. 5, 1974, pp. 1-5.

Enders et al., "Propagation in Tissue Cultures of Cytopathogenic Agents from Patients with Measles", Proceedings of the Society for Experimental Biology and Medicine, vol. 86, 1954, pp. 277-286.

Erbs et al., "Modified Vaccinia Virus Ankara as a Vector for Suicide Gene Therapy", Cancer Gene Therapy, vol. 15, 2008, pp. 18-28.

Gerna et al., "Dendritic-Cell Infection by Human Cytomegalovirus is Restricted to Strains Carrying Functional UL131-128 Genes and Mediates Efficient Viral Antigen Presentation to CD8 + T Cells", Journal of General Virology, vol. 86, 2005, pp. 275-284.

Gerna et al., "Human Cytomegalovirus Serum Neutralizing Antibodies Block Virus Infection of Endothelial/Epithelial Cells, But Not Fibroblasts, Early During Primary Infection", Journal of General Virology, vol. 89, 2008, pp. 853-865.

Gerna et al., "Rescue of Human Cytomegalovirus Strain AD169 Tropism for both Leukocytes and Human Endothelial Cells", Journal of General Virology, vol. 84, 2003, pp. 1431-1436.

Gerna et al., "The Attenuated Towne Strain of Human Cytomegalovirus may Revert to both Endothelial Cell Tropism and Leuko- (Neutrophil- and Monocyte-) Tropism In Vitro", Journal of General Virology, vol. 83, 2002, pp. 1993-2000.

Hahn et al., "Human Cytomegalovirus UL131-128 Genes Are Indispensable for Virus Growth in Endothelial Cells and Virus Transfer to Leukocytes", Journal of Virology, vol. 78, No. 18, Sep. 2004, pp. 10023-10033.

Hermiston, Terry, "Gene Delivery from Replication-Selective Viruses: Arming Guided Missiles in the War Against Cancer", The Journal of Clinical Investigation, vol. 105, No. 9, May 2000, pp. 1169-1172.

Hilleman et al., "Development and Evaluation of the Moraten Measles Virus Vaccine", The Journal of the American Medical Association, vol. 206, No. 3, 1968., pp. 587-590.

International Preliminary Report on Patentability received for PCT Patent Application No. PCT/IB2016/000993, dated Dec. 28, 2017, 8 pages.

International Search Report and Written Opinion received for PCT Patent Application No. PCT/IB2016/000993, dated Dec. 8, 2016, 11 pages.

Jelic et al., "Hepatocellular Carcinoma: ESMO Clinical Practice Guidelines for Diagnosis, Treatment and Follow-up", Annals of Oncology, vol. 21, Issue. 5, 2010, pp. v59-v64.

Kerr et al., "Immune Responses to Myxoma Virus", Viral Immunology, vol. 15, No. 2, 2002, pp. 229-246.

Llovet et al., "Arterial Embolisation or Chemoembolisation Versus Symptomatic Treatment in Patients with Unresectable Hepatocellular Carcinoma: A Randomised Controlled Trial", The Lancet, vol. 359, May 18, 2002, pp. 1734-1739.

Macagno et al., "Isolation of Human Monoclonal Antibodies That Potently Neutralize Human Cytomegalovirus Infection by Targeting Different Epitopes on the gH/gL/UL128-131A Complex", Journal of Virology, vol. 84, No. 2, Jan. 2010, pp. 1005-1013.

(56) References Cited

OTHER PUBLICATIONS

Nakamura et al., "Five-Year Survival after Transcatheter Chemoembolization for Hepatocellular Carcinoma", Cancer Chemotherapy and Pharmacology, vol. 33, 1994, pp. S89-S92.
Okada et al., "Antitumoral Efficacy and Pharmacokinetic Properties of Pirarubicin Upon Hepatic Intra-Arterial Injection in the Rabbit VX2 Tumor Model", British Journal of Cancer, vol. 71, 1995, pp. 518-524.
Plachter et al., "Cell Types Involved in Replication and Distribution of Human Cytomegalovirus", Advances in Virus Research, vol. 46, 1996, pp. 195-261.
Plotkin et al., "Candidate Cytomegalovirus Strain for Human Vaccination", Infection and Immunity, vol. 12, No. 3, Sep. 1975, pp. 521-527.
Revello et al., "Molecular Epidemiology of Primary Human Cytomegalovirus Infection in Pregnant Women and Their Families", Journal of Medical Virology, vol. 80, 2008, pp. 1415-1425.
Robbins et al., "Inhibition of Measles Virus Replication by Cyclic AMP", Virology, vol. 106, 1980, pp. 317-326.
Ryckman et al., "Characterization of the Human Cytomegalovirus gH/gL/UL128-131 Complex That Mediates Entry into Epithelial and Endothelial Cells", Journal of Virology, vol. 82, No. 1, Jan. 2008, pp. 60-70.
Senzer et al., "Phase II Clinical Trial of a Granulocyte-Macrophage Colony-Stimulating Factor-Encoding, Second-Generation Oncolytic Herpesvirus in Patients with Unresectable Metastatic Melanoma", Journal of Clinical Oncology, vol. 27, No. 34, Dec. 1, 2009, pp. 5763-5771.
Shinozaki et al., "Oncolysis of Multifocal Hepatocellular Carcinoma in the Rat Liver by Hepatic Artery Infusion of Vesicular Stomatitis Virus", Molecular Therapy, vol. 9, No. 3, Mar. 2004, pp. 368-376.
Sinitsyna et al., "Further-Attenuated Measles Vaccine: Virus Passages affect Viral Surface Protein Expression, Immunogenicity and Histopathology Pattern in Vivo", Research in Virology, vol. 141, 1990, pp. 517-531.
Sinkovics et al., "Newcastle Disease Virus (NDV): Brief History of its Oncolytic Strains", Journal of Clinical Virology, vol. 16, 2000, pp. 1-15.
Sze et al., "Oncolytic Virotherapy", Journal of Vascular and Interventional Radiology, vol. 24, No. 8, Aug. 2013, pp. 1115-1122.
Takeda et al., "Measles Virus Attenuation Associated with Transcriptional Impediment and a Few Amino Acid Changes in the Polymerase and Accessory Proteins", Journal of Virology, vol. 72, No. 11, Nov. 1998, pp. 8690-8696.
Takehara et al., "Characterization of Baculovirus-Expressed Hemagglutinin and Fusion Glycoproteins of the Attenuated Measles Virus Strain AIK-C", Virus Research, vol. 26, 1992, pp. 167-175.
Todo et al., "In Situ Expression of Soluble B7-1 in the Context of Oncolytic Herpes Simplex Virus Induces Potent Antitumor Immunity", Cancer Research, vol. 61, Jan. 1, 2001, pp. 153-161.
Vermeer et al., "Vaccinia Virus Entry, Exit, and Interaction with Differentiated Human Airway Epithelia", Journal of Virology, vol. 81, No. 18, Sep. 2007, pp. 9891-9899.
Wang et al., "Human Cytomegalovirus UL131 Open Reading Frame is Required for Epithelial Cell Tropism", Journal of Virology, vol. 79, No. 16, Aug. 2005, pp. 10330-10338.
Wang et al., "Human Cytomegalovirus Virion Protein Complex required for Epithelial and Endothelial Cell Tropism", PNAS, vol. 102, No. 50, Dec. 13, 2005, pp. 18153-18158.
Yoon et al., "Transcatheter Arterial Chemoembolization with Paclitaxel-Lipiodol Solution in Rabbit VX2 Liver Tumor1", Radiology, vol. 229, No. 1, Oct. 2003, pp. 126-131.

\* cited by examiner

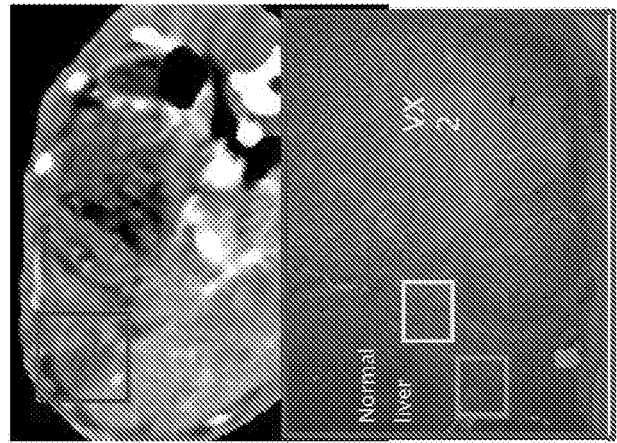
FIG. 3B
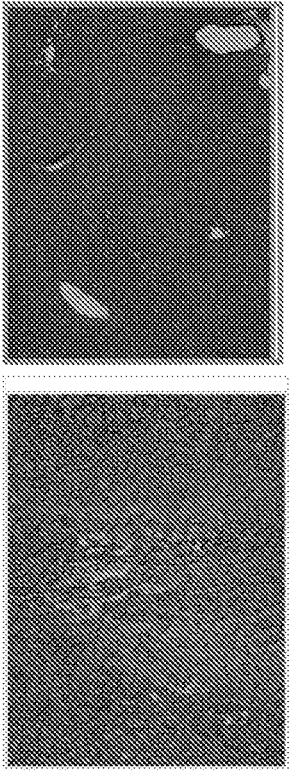
FIG. 3E
FIG. 3D
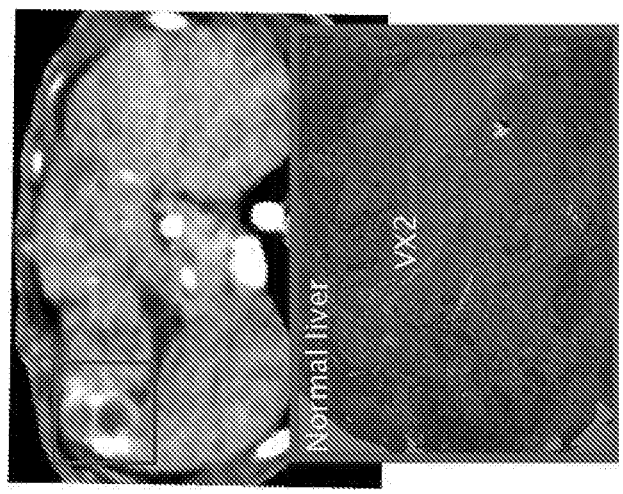
FIG. 3A
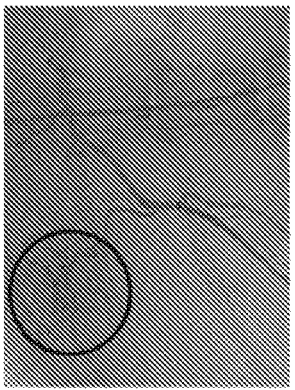
FIG. 3C

COMPOSITIONS AND METHODS FOR VIRAL EMBOLIZATION

CROSS-REFERENCE TO RELATED APPLICATIONS

This application is a U.S. National Phase Patent Application of PCT/IB2016/000993, filed Jun. 17, 2016, which claims priority to U.S. Provisional Patent Application No. 62/182,383, filed Jun. 19, 2015, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737562000100SEQLIST.txt, date recorded: Jan. 16, 2018, size: 2 KB).

FIELD

The present disclosure relates to compositions and methods related to transarterial embolization with oncolytic viruses.

BACKGROUND

Therapeutic vascular occlusion (embolization) is a technique used to treat pathological conditions in situ by injection of an occlusion agent (embolic material) into a vessel. Embolization is carried out by means of catheters, making it possible to position particulate occlusion agents or gels (emboli) in the circulatory system. In active embolization therapy, embolic agents are formulated with therapeutic agents, such as a drug or chemotherapeutic, resulting in both mechanical blockage and in situ delivery of the therapeutic agent. The use of embolization in cancer therapy has also been established. For example, blood vessels which nourish cancerous tumors are deliberately blocked by injection of an embolic material into the vessel. Vascular occlusion can limit blood loss during the surgical interventions, and contribute to tumoral necrosis and recession. Combining the occlusion agent with a chemotherapeutic can allow delivery of the chemotherapeutic directly to the tumor without significant systemic deliverly, which allows higher doses of chemotherapeutic to be used.

Transarterial embolization (TAE) or transarterial chemo-embolization (TACE) have been used extensively to treat patients with hypervascular tumors confined to the liver or tumors where the intrahepatic component is the main source of mobidity and mortality. TAE/TACE are considered effective palliative care for unresectable tumors or as an adjuvant to manage postoperative recurrent tumors (Camma et al, (2002) *Radiology*, 224:47-54; Llovet et al., (2002) *Lancet* 359:1734-1739; Jelic et al., (2010) *Ann Oncol.* 21 Suppl 5:v59-v64). Various embolization agents and chemotherapeutics have been used, although clear superiority for any particular regimen or chemotherapeutic has not been demonstrated (Nakamura et al., (1994) *Cancer Chemother Pharmacol* 33 Suppl:S89-S92; Bruix et al., (2004) *Gastroenterology* 127:S179-S188).

In parallel, oncolytic viruses are in development for treatment of cancer. For example, replication-selective oncolytic viruses hold promise for the treatment of cancer (Kim et al., (2001) *Nat. Med.*, 7(7):781-787). These viruses can cause tumor cell death through direct replication-dependent and/or viral gene expression-dependent oncolytic effects (Kirn et al., (2001) *Nat. Med.*, 7(7):781-787). In addition, viruses are able to enhance the induction of cell-mediated antitumor immunity within the host (Todo et al., (2001) *Cancer Res.*, 61:153-161; Sinkovics et al., (2000) *J. Clin. Viro.*, 16:1-15). These viruses also can be engineered to expressed therapeutic transgenes within the tumor to enhance antitumor efficacy (Hermiston, (2000) *J. Clin. Invest.*, 105:1169-1172).

However, major limitations exist to this therapeutic approach. Although a degree of natural tumor-selectivity can be demonstrated for some virus species, new approaches are still needed to engineer and/or enhance tumor-selectivity for oncolytic viruses in order to maximize safety and efficacy. This selectivity is particularly important when intravenous administration is used, and when potentially toxic therapeutic genes are added to these viruses to enhance antitumor potency; gene expression will need to be tightly limited in normal tissues. In addition, increased antitumor potency through additional mechanisms such as induction of antitumor immunity or targeting of the tumor-associated vasculature is highly desirable. Therefore, more effective and less toxic therapies for the treatment of cancer are needed.

Initial attempts to combine oncolytic viral therapy with embolization have been made. An oncolytic form of vesicular stomatitis virus (VSV) has been tested in tumor models (Altomonte et al. (2008) *Hepatology* 48:1864-1873). VSV was an ideal candidate to test with embolization. VSV, a member of the rhabdoviridae family, is a negative-sense RNA virus 180 nm long and 75 nm wide. VSV enters and is released from the basolateral surfaces of polarized cells. The basolateral release of VSV allows it to readily infect underlying tissues, including tumor tissues (Basak et al., (1989) *J. Virology*, 63(7):3164-3167). In addition, the small size of VSV, particularly the 75 nm diameter of its smallest axis, allows its passage through the leaky junctions between blood vessel cells, allowing the infection of underlying tissues and through the basolateral surface of the blood vessel cells. Due to its small size and basal surface budding, one of skill in the art could have expected successful infection of tumor tissue during viral embolization of VSV.

Given the ideal characteristics of VSV, it is difficult to extrapolate other oncolytic viruses. For example, viruses that that have a diameter along their smallest axis that is larger than the junctions between cells of blood vessels may not be able to pass from the blood stream to the surrounding issue. Similarly, viruses that release from the apical side of polar cells are typically limited to infection along epithelial cell linings (Basak et al. (1989) *J. Virology*, 63(7):3164-3167). When such a virus infects a polar endothelial blood vessel cell, the replicated viruses could simply be released back into the blood stream rather than into the underlying tissue if released apically. Vaccinia virus is an example of a virus that has a number of undesirable characteristics that could have been expected to prevent effective embolization. Vaccinia virus (VV), a member of the poxvirus family, is a large virus roughly 360 nm by 250 nm in size. Vaccinia virus preferentially infects through the basolateral surface of polar cells, but its viral progeny are released from the apical surface (Vermeer et al., (2007) *J. Virology*, 81(18):9891-9899). A virus that is apically released from the polar endothelial cells that create the blood vessel waslls is thus at risk of being washed away by the blood stream. In addition, due to its large size, vaccinia virus would have difficulty passing through cellular junctions between cells of the blood vessel walls to reach to the basolateral surface of the endothelial cells and subsequently infect underlying tissues in any substantial amount. Based upon its lifecycle and size, one could not extrapolate from the VSV results to oncolytic vaccinia virus, or other large viruses or viruses that release from the apical surface for that matter, being able to achieve a significant penetration into a tumor during vascular embolization.

All references cited herein, including patent applications and publications, are hereby incorporated by reference in their entirety.

SUMMARY

Some aspects of this invention are based upon the discovery that oncolytic vaccina viruses, despite the size and the apical release from polarized cells, as an exemplary oncolytic virus, can be used in a surprisingly effective manner in combination with embolization therapy.

An aspect of the invention includes compositions comprising an oncolytic Poxviridae, Herpesviridae, or Measles virus and a biocompatible microparticle or hydrophilic polymer gel agent suitable for active embolization. In some embodiments, the oncolytic virus is a Poxviridae virus selected from the group consisting of: vaccinia virus, myxomavirus, and parapoxvirus. In some embodiments, the oncolytic virus is an oncolytic vaccinia virus. In some embodiments, the oncolytic vaccinia virus does not comprise an active thymidine kinase gene. In some embodiments, which may be combined with any of the preceding embodiments that include an oncolytic vaccinia virus, the oncolytic vaccinia virus does not comprise an active vaccinia growth factor (VGF) gene. In certain embodiments, which can be combined with any of the preceding embodiments that include an oncolytic vaccinia virus, the oncolytic vaccinia virus comprises transgenes encoding *Renilla* luciferase, green fluorescent protein, β-galactosidase, and β-glucuronidase. In certain embodiments, which can be combined with any of the preceding embodiments that include an oncolytic vaccinia virus, the oncolytic vaccinia virus is a Copenhagen strain, a Western Reserve strain, a Wyeth strain, or a Lister strain. In certain embodiments, which can be combined with any of the preceding embodiments that include an oncolytic vaccinia virus, the oncolytic vaccinia virus further comprises one of more of a granulocyte-macrophage colony stimulating factor protein, a cytosine deaminase protein, and a somatostatin receptor type 2 protein. In some embodiments, the oncolytic virus is a Herpesviridae virus selected from the group consisting of: herpes simplex virus-1, herpes simplex virus-2, and cytomegalovirus. In some embodiments, the oncolytic virus is a herpes simplex virus 1. In certain embodiments, the herpes simplex virus-1 is derived from strain JS-1. In certain embodiments, which can be combined with any of the preceding embodiments that include a herpes simplex virus-1, the herpes simplex virus-1 has one or more of: an inactivated ICP34.5 gene, an inactivated ICP45 gene, an earlier insertion of the US11 gene, an inactivated ICP6 gene, a human granulocyte-macrophage colony stimulating factor gene, and a nitroreductase gene. In certain embodiments, which can be combined with any of the preceding embodiments that include a herpes simplex virus-1, the herpes simplex virus-1 has an inactivated ICP34.5 gene, an inactivated ICP45 gene, and a human granulocyte-macrophage colony stimulating factor gene. In some embodiments, oncolytic virus is a myxomavirus. In some embodiments, the myxomavirus is derived from strain Lausanne. In certain embodiments, which can be combined with any of the preceding embodiments that include a myxomavirus, the myxomavirus has one or more inactivated genes selected from: M010L, M011L, M-T5, M151R, M001R, M152R, M153R, M154L, M156R, M008.1R, M008R, M007R, M006R, M005R, M004.1R, M004R, M003.2R, M003.1R, and M002R. In some embodiments, the oncolytic virus is a parapoxvirus. In some embodiments, the parapoxvirus is derived from an orf virus strain. In some embodiments, the orf strain is selected from OV NZ-2, OV NZ-7, and OV-SA00. In certain embodiments, which can be combined with any of the preceding embodiments that include a parapoxvirus, the parapoxvirus has an insertion of one or more heterologous host range genes. In some embodiments, the heterologous host range genes are selected from SPI-1, SPI-2, KIL, C7L, p28/N1R, B5R, E3L, K3L, M-T2, M-T4, M-T5, M11L, M13L, M063, and F11L. In some embodiments, the oncolytic virus is Measles virus. In some embodiments, the Measles virus is derived from an Edmonston, Moraten, Leningrad, Moscow, or Schwarz strain. In certain embodiments, which can be combined with any of the preceding embodiments that include a Measles virus, the Measles virus has an insertion of a gene encoding human thyroidal sodium iodide symporter (NIS). In certain embodiments, which can be combined with any of the preceding embodiments, the oncolytic virus is at least 0.1 µm in diameter along its shortest axis. In certain embodiments, which can be combined with any of the preceding embodiments, the oncolytic virus is at least 0.2 µm in diameter along its shortest axis. In certain embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In certain embodiments, which can be combined with any of the preceding embodiments, the microparticles of the biocompatible microparticle agent are between 100 µm and 2000 µm, between 150 µm and 350 µm, between 150 µm and 200 µm, between 200 µm and 250 µm in size, between 250 µm and 300 µm, or between 300 µm and 350 µm in size. In certain embodiments, which can be combined with any of the preceding embodiments, individual particles of the biocompatible microparticle agent vary in size from about 0 µm to about 100 µm, from about 0 µm to about 50 µm, or from about 0 µm to about 25 µm. In certain embodiments, which can be combined with any of the preceding embodiments, individual particles of the biocompatible microparticle agent have an average difference in diameter of 100 µm or less, about 50 µm or less, about 25 µm or less, about 10 µm or less or about 5 µm or less. In certain embodiments, which can be combined with any of the preceding embodiments, individual particles of the biocompatible microparticle agent are aggregates of particulates that are between 10 and 200 µm or between 10 and 100 µm. In certain embodiments, which can be combined with any of the preceding embodiment that include a hydrophilic polymer gel agent, the hydrophilic polymer gel agent comprises particulates that are between 10 and 200 µm or between 10 and 100 µm. In certain embodiments, which can be combined with any of the preceding embodiments, the biocompatible microparticle or hydrophilic polymer gel agent is a temporary embolic agent or a permanent embolic agent.

Another aspect of the invention includes compositions comprising an oncolytic virus at least 0 µm in diameter along the shortest axis of the virus and a biocompatible microparticle or hydrophilic polymer gel suitable for active embolization. In some embodiments, the oncolytic virus is at least 0.15 µm, or at least 0.2 µm in diameter along its shortest axis.

In some embodiments, the oncolytic virus is from 0.1-0.2 µm, from 0.2-0.3 µm, from 0.3-0.4 µm, from 0.4-0.5 µm, from 0.5-0.6 µm, from 0.6-0.7 µm, from 0.1-0.7 µm, from 0.15-0.7 µm, or from 0.2-0.7 µm in diameter along the shortest axis of the virus. In certain embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In certain embodiments, which can be combined with any of the preceding embodiments, the microparticles of the biocompatible microparticle agent are between 100 µm and 2000 µm, between 150 µm and 350 µm, between 150 µm and 200 µm, between 200 µm and 250 µm in size, between 250 µm and 300 µm, or between 300 µm and 350 µm in size. In certain embodiments, which can be combined with any of the preceding embodiments, individual particles of the biocompatible microparticle agent vary in size from about 0 µm to about 100 µm, from about 0 µm to about 50 µm, or from about 0 µm to about 25 µm. In certain embodiments, which can be combined with any of the preceding embodiments, individual particles of the biocompatible microparticle agent have an average difference in diameter of 100 µm or less, about 50 µm or less, about 25 µm or less, about 10 µm or less or about 5 µm or less. In certain embodiments, which can be combined with any of the preceding embodiments, individual particles of the biocompatible microparticle agent are aggregates of particulates that are between 10 and 200 µm or between 10 and 100 µm. In certain embodiments, which can be combined with any of the preceding embodiment that include a hydrophilic polymer gel agent, the hydrophilic polymer gel agent comprises particulates that are between 10 and 200 µm or between 10 and 100 µm. In certain embodiments, which can be combined with any of the preceding embodiments, the biocompatible microparticle or hydrophilic polymer gel agent is a temporary embolic or a permanent embolic agent.

Yet another aspect of the invention includes compositions comprising an oncolytic virus that buds from an apical surface of an infected polarized cell and a biocompatible microparticle or hydrophilic polymer gel agent suitable for active embolization. In certain embodiments, the oncolytic virus is at least 0.1 µm in diameter along its shortest axis. In certain embodiments, which can be combined with any of the preceding embodiments, the oncolytic virus is at least 0.2 µm in diameter along its shortest axis. In certain embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In certain embodiments, which can be combined with any of the preceding embodiments, the microparticles of the biocompatible microparticle agent are between 100 µm and 2000 µm, between 150 µm and 350 µm, between 150 µm and 200 µm, between 200 µm and 250 µm in size, between 250 µm and 300 µm, or between 300 µm and 350 µm in size. In certain embodiments, which can be combined with any of the preceding embodiments, individual particles of the biocompatible microparticle agent vary in size from about 0 µm to about 100 µm, from about 0 µm to about 50 µm, or from about 0 µm to about 25 µm. In certain embodiments, which can be combined with any of the preceding embodiments, individual particles of the biocompatible microparticle agent have an average difference in diameter of 100 µm or less, about 50 µm or less, about 25 µm or less, about 10 µm or less or about 5 µm or less. In certain embodiments, which can be combined with any of the preceding embodiments, individual particles of the biocompatible microparticle agent are aggregates of particulates that are between 10 and 200 µm or between 10 and 100 µm. In certain embodiments, which can be combined with any of the preceding embodiment that include a hydrophilic polymer gel agent, the hydrophilic polymer gel agent comprises particulates that are between 10 and 200 µm or between 10 and 100 µm. In certain embodiments, which can be combined with any of the preceding embodiments, the biocompatible microparticle or hydrophilic polymer gel agent is a temporary embolic agent or a permanent embolic agent.

Still another aspect of the invention includes compositions comprising an oncolytic virus and a biocompatible microparticle or hydrophilic polymer gel agent suitable for active embolization, wherein the biocompatible microparticle or hydrophilic polymer gel agent increases the viral output from tumor cells cultured in vitro by at least 50%. In some embodiments, the biocompatible microparticle or hydrophilic polymer gel agent increases the viral output from tumor cells cultured in vitro by at least 75%, at least 100%, at least 150%, at least 200% or at least 300%. In some embodiments, the biocompatible microparticle or hydrophilic polymer gel agent increases the viral output from tumor cells cultured in vitro by between 50% and 400%, between 75% and 400%, between 100% and 400%, between 150% and 400%, between 200% and 400%, or between 300% and 400%. In certain embodiments, which can be combined with any of the preceding embodiments, the composition comprises an oncolytic Poxviridae, Herpesviridae, or Measles virus and a biocompatible microparticle or hydrophilic polymer gel agent suitable for active embolization. In some embodiments, the oncolytic virus is a Poxviridae virus selected from the group consisting of: vaccinia virus, myxomavirus, and parapoxvirus. In some embodiments, the oncolytic virus is an oncolytic vaccinia virus. In some embodiments, the oncolytic vaccinia virus does not comprise an active thymidine kinase gene. In some embodiments, which may be combined with any of the preceding embodiments that include an oncolytic vaccinia virus, the oncolytic vaccinia virus does not comprise an active vaccinia growth factor (VGF) gene. In certain embodiments, which can be combined with any of the preceding embodiments that include an oncolytic vaccinia virus, the oncolytic vaccinia virus comprises transgenes encoding *Renilla* luciferase, green fluorescent protein, β-galactosidase, and β-glucuronidase. In certain embodiments, which can be combined with any of the preceding embodiments that include an oncolytic vaccinia virus, the oncolytic vaccinia virus is a Copenhagen strain, a Western Reserve strain, a Wyeth strain, or a Lister strain. In certain embodiments, which can be combined with any of the preceding embodiments that include an oncolytic vaccinia virus, the oncolytic vaccinia virus further comprises one of more of a granulocyte-macrophage colony stimulating factor protein, a cytosine deaminase protein, and somatostatin receptor type 2 protein. In some embodiments, the oncolytic virus is a Herpesviridae virus selected from the group consisting of: herpes simplex virus-1, herpes simplex virus-2, and cytomegalovirus. In some embodiments, the oncolytic virus is a herpes simplex virus 1. In certain embodiments, the herpes simplex virus-1 is derived from strain JS-1. In certain embodiments, which can be combined with any of the preceding embodiments that include a herpes simplex virus-1, the herpes simplex virus-1 has one or more of: an inactivated ICP34.5 gene, an inactivated ICP45 gene, an earlier insertion of the US11 gene, an inactivated ICP6 gene, a human granulocyte-macrophage colony stimulating factor gene, and a nitroreductase gene. In certain embodiments, which can be combined with any of the preceding embodiments that include a herpes simplex virus-1, the herpes simplex virus-1 has an inactivated ICP34.5 gene, an inactivated ICP45 gene, and a human granulocyte-macrophage colony stimulating factor gene. In some embodiments, oncolytic virus is a myxomavirus. In some embodiments, the myxomavirus is derived from strain Lausanne. In certain embodiments, which can be combined with any of the preceding embodiments that include a myxomavirus, the myxomavirus has one or more inactivated genes selected from: M010L, M011L, M-T5, M151R, M001R, M152R, M153R, M154L, M156R, M008.1R, M008R, M007R, M006R, M005R, M004.1R, M004R, M003.2R, M003.1R, and M002R. In some embodiments, the oncolytic virus is a parapoxvirus. In some embodiments, the parapoxvirus is derived from an orf virus strain. In some embodiments, the orf strain is selected from OV NZ-2, OV NZ-7, and OV-SA00. In certain embodiments, which can be combined with any of the preceding embodiments that include a parapoxvirus, the parapoxvirus has an insertion of one or more heterologous host range genes. In some embodiments, the heterologous host range genes are selected from SPI-1, SPI-2, KIL, C7L, p28/N1R, B5R, E3L, K3L, M-T2, M-T4, M-T5, M11L, M13L, M063, and F11L. In some embodiments, the oncolytic virus is Measles virus. In some embodiments, the Measles virus is derived from an Edmonston, Moraten, Leningrad, Moscow, or Schwarz strain. In certain embodiments, which can be combined with any of the preceding embodiments that include a Measles virus, the Measles virus has an insertion of a gene encoding human thyroidal sodium iodide symporter (NIS). In certain embodiments, which can be combined with any of the preceding embodiments, the oncolytic virus is at least 0.1 µm in diameter along its shortest axis. In certain embodiments, which can be combined with any of the preceding embodiments, the oncolytic virus is at least 0.2 µm in diameter along its shortest axis. In certain embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In certain embodiments, which can be combined with any of the preceding embodiments, the microparticles of the biocompatible microparticle agent are between 100 µm and 2000 µm, between 150 µm and 350 µm, between 150 µm and 200 µm, between 200 µm and 250 µm in size, between 250 µm and 300 µm, or between 300 µm and 350 µm in size. In certain embodiments, which can be combined with any of the preceding embodiments, individual particles of the biocompatible microparticle agent vary in size from about 0 µm to about 100 µm, from about 0 µm to about 50 µm, or from about 0 µm to about 25 µm. In certain embodiments, which can be combined with any of the preceding embodiments, individual particles of the biocompatible microparticle agent have an average difference in diameter of 100 µm or less, about 50 µm or less, about 25 µm or less, about 10 µm or less or about 5 µm or less. In certain embodiments, which can be combined with any of the preceding embodiments, individual particles of the biocompatible microparticle agent are aggregates of particulates that are between 10 and 200 µm or between 10 and 100 µm. In certain embodiments, which can be combined with any of the preceding embodiment that include a hydrophilic polymer gel agent, the hydrophilic polymer gel agent comprises particulates that are between 10 and 200 µm or between 10 and 100 µm. In certain embodiments, which can be combined with any of the preceding embodiments, the biocompatible microparticle or hydrophilic polymer gel agent is a temporary embolic agent or a permanent embolic agent.

Another aspect of the invention includes methods for active embolization of a vascular site in a mammal, comprising introducing into the vascular site of the mammal the compositions of any of the preceding four aspects and any of their embodiments and combinations of embodiments. In certain embodiments, the vascular site is in a tumor, supplies blood to the tumor, or is proximal to the tumor. In some embodiments, the tumor is in the liver. In certain embodiments, which can be combined with any of the proceding embodiments, the tumor is a primary tumor or a secondary tumor. In certain embodiments, the secondary tumor is a metastasized malignant melanoma. In some embodiments, the tumor is in the liver. In certain embodiments, which can be combined with any of the proceding embodiments, the mammal is a human. In certain embodiments, which can be combined with any of the proceding embodiments, a contrast agent is introduced into the vasculature. In certain embodiments, the contrast agent is selected from: metrizamide, iopamidol, iodixanol, iohexol, iopromide, iobtiridol, iomeprol, iopentol, iopamiron, ioxilan, iotrolan, gadodiamide, gadoteridol, iotrol, ioversol, or combinations thereof.

Yet another aspect of the invention includes methods for treating cancer by debulking a tumor mass, comprising introducing into a vascular site of a mammal the compositions of any preceding four composition related aspects and any of their embodiments and combinations of embodiments, wherein the method induces necrosis in at least 75% of the embolized tumor mass. In certain embodiments, the method induces necrosis in at least 85% of the embolized tumor mass, at least 90% of the embolized tumor mass, or even at least 95% of the embolized tumor mass. In certain embodiments, which can be combined with any of the preceding embodiments, the vascular site is in a tumor, supplies blood to the tumor, or is proximal to the tumor. In some embodiments, the tumor is in the liver. In certain embodiments, which can be combined with any of the proceding embodiments, the tumor is a primary tumor or a secondary tumor. In certain embodiments, the secondary tumor is a metastasized malignant melanoma. In some embodiments, the tumor is in the liver. In certain embodiments, which can be combined with any of the proceding embodiments, the mammal is a human. In certain embodiments, which can be combined with any of the proceding embodiments, a contrast agent is introduced into the vasculature. In certain embodiments, the contrast agent is selected from: metrizamide, iopamidol, iodixanol, iohexol, iopromide, iobtiridol, iomeprol, iopentol, iopamiron, ioxilan, iotrolan, gadodiamide, gadoteridol, iotrol, ioversol, or combinations thereof.

Still another aspect of the invention includes methods for active embolization of a vascular site in a mammal, comprising introducing into the vascular site of the mammal a composition comprising an oncolytic virus and a biocompatible microparticle or hydrophilic polymer gel agent suitable for active embolization, wherein the mammal one day after the introducing step has less than 10 pfu of the oncolytic virus per ml of blood. In certain embodiments, the compositions may be any of the preceding four composition related aspects and any of their embodiments and combinations of embodiments. In certain embodiments, the mammal one day after the introducing step has less than 5 pfu of the oncolytic virus per ml of bloodor even less than 2 pfu of the oncolytic virus per ml of blood. In certain embodiments, which can be combined with any of the preceding embodiments, the vascular site is in a tumor, supplies blood to the tumor, or is proximal to the tumor. In some embodiments, the tumor is in the liver. In certain embodiments, which can be combined with any of the proceding embodiments, the tumor is a primary tumor or a secondary tumor. In certain embodiments, the secondary tumor is a metastasized malignant melanoma. In some embodiments, the tumor is in the liver. In certain embodiments, which can be combined with any of the proceding embodiments, the mammal is a human. In certain embodiments, which can be combined with any of the proceding embodiments, a contrast agent is introduced into the vasculature. In certain embodiments, the contrast agent is selected from: metrizamide, iopamidol, iodixanol, iohexol, iopromide, iobtiridol, iomeprol, iopentol, iopamiron, ioxilan, iotrolan, gadodiamide, gadoteridol, iotrol, ioversol, or combinations thereof.

It is to be understood that one, some, or all of the properties of the various embodiments described herein may be combined to form other embodiments of the present disclosures. These and other aspects of the disclosure will become apparent to one of skill in the art.

BRIEF DESCRIPTION OF THE FIGURES

FIG. 3 shows representative CT and histological staining images of liver tissue from a control animal (FIG. 3A) and an animal treated with Gelfoam formulated Pexa-Vec (FIG. 3B). FIG. 3C shows a representative angiography image of bile ducts from an animal treated with Gelfoam formulated Pexa-Vec. FIGS. 3D&E show representative H&E stained images of the junction between normal liver and tumor tissues (FIG. 3D) and normal liver parenchyma (FIG. 3E) in an animal treated with Gelfoam formulated Pexa-Vec.

DETAILED DESCRIPTION OF PREFERRED EMBODIMENTS

Figure 1B:
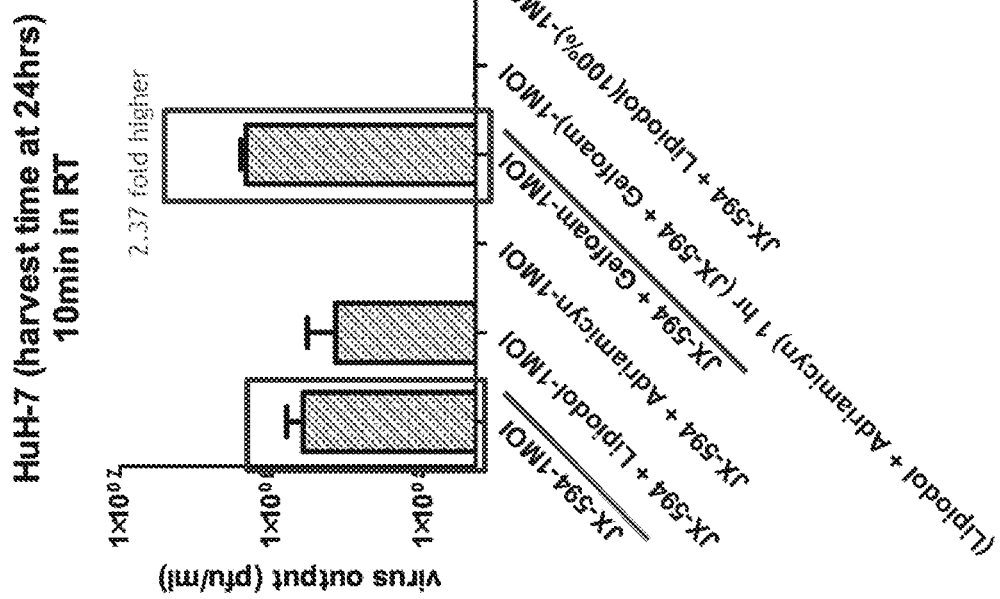
FIG. 1 shows viral output of HuH-7 cells infected with JX-594 virus pre-incubated with Lipiodol, Adriamicyn, and/or Gelfoam. Viral output was measured in cell culture supernatants collected at 24 (FIGS. 1A&B) and 48 (FIGS. 1C&D) hours post infection at an MOI of 100 (FIGS. 1A&C) or 1 (FIGS. 1B&D).

Certain aspects of the inventions disclosed herein are based upon the surprising discovery that oncolytic vaccinia virus can effectively be administered by transarterial embolization techniques despite its large size and suboptimal basolateral infection and apical release from epithelial cells such as the cells forming blood vessel walls. Based upon this surprising discovery one can readily extrapolate to other oncolytic viruses of the same size and smaller and to other oncolytic viruses of similarly suboptimal life cycles. Exemplary oncolytic viruses include double stranded DNA viruses such as Poxviridae viruses and herpes viruses, viruses larger than 100 nm in along their smalles axis, and viruses the bud from the apical membrane of polar cells such as blood vessel endothelial cells.

Certain aspects of the inventions disclosed herein are based upon other surprising improvements over prior art direct tumoral injection and trans-arterial oncolytic VSV embolization including, without limitation, the lack of oncolytic virus from the claimed compositions and methods seeping into the blood stream. Preferably, after introducing or administering the oncolytic virus as disclosed herein, the subject will have one day after administration less than 10 pfu of the oncolytic virus per ml of blood, less than 5 pfu of the oncolytic virus per ml of blood, or less than 2 pfu of the oncolytic virus per ml of blood.

An aspect of embolization with the oncolytic viruses as disclosed in this specification is to debulk the tumor mass using virus-mediated killing of tumor cells much more effectively than through either transarterial embolization or direct tumoral injection of oncolytic virus alone. In preferred embodiments, the embolization with the oncolytic viruses as disclosed in this specification debulk the tumor mass using virus-mediated killing of tumor cells much more effectively than through any of transarterial embolization, transarterial chemoembolization, transarterial radioembolization, or direct tumoral injection of oncolytic virus alone. The oncolytic viruses of the disclosure, when delivered with an embolizing agent, are retained in the tumor microenvironment, thereby allowing more viral infection of cancer cells and preventing oncolytic virus from entering the blood stream. Transient vascular shut down and viral replication subsequently result in tumor necrosis throughout the tumor microenvironment, not just the tumor environment local to the vaculature, thereby 'debulking' the tumor mass without observable damage to the surrounding healthy tissue. In preferred embodiments, the method of debulking results in necrosis of at least 75%, at least 80%, at least 85%, at least 90%, or at least 95% of the embolized tumor mass. In one aspect, the disclosure provides compositions containing an oncolytic virus and a biocompatible microparticle or hydrophilic polymer gel suitable for active embolization. In another aspect, the disclosure provides a method for active embolization of a vascular site in a mammal by introducing into the vasculature of a mammal an oncolytic virus and a biocompatible microparticle or hydrophilic polymer gel suitable for active embolization.

Oncolytic Viruses

The compositions and methods disclosed in this specification will involve oncolytic viruses other than VSV. Exemplary oncolytic viruses include double stranded DNA viruses such as pox viruses and herpes viruses. A preferred oncolytic virus is vaccinia virus. In one aspect, the oncolytic virus buds from an apical surface of an infected polarized cell. In a preferred embodiment, the oncolytic virus that buds from an apical surface of an infected polarized cell is oncolytic vaccinia virus. In another aspect, which may be combined with any of the preceding aspects, the oncolytic virus is at least 0.1 µm in diameter along the shortest axis of the virus. In one embodiment, the oncolytic virus is at least 0.1 µm, at least 0.15 µm, or at least 0.2 µm in diameter along its shortest axis. The oncolytic virus may be from 0.1-0.2 µm, from 0.2-0.3 µm, from 0.3-0.4 µm, from 0.4-0.5 µm, from 0.5-0.6 µm, from 0.6-0.7 µm, from 0.1-0.7 µm, from 0.15-0.7 µm, or from 0.2-0.7 µm in diameter along the shortest axis of the virus.

A. Oncolytic Vaccinia Virus

In a preferred embodiment, the oncolytic virus is a Poxviridae virus, such as oncolytic vaccinia virus. Vaccinia virus (VV) is a complex enveloped virus having a linear double-stranded DNA genome of about 190K bp and encoding for approximately 250 genes. Vaccinia virus is a large virus roughly 360 nm by 250 nm in size. Vaccinia is well-known for its role as a vaccine that eradicated smallpox. Post-eradication of smallpox, scientists have been exploring the use of vaccinia as a tool for delivering genes into biological tissues in gene therapy and genetic engineering applications.

Vaccinia virus preferentially infects through the basolateral surface of cells, but its viral progeny are released from the apical surface. Polarized cells include, without limitation, epithelial cells, endothelial cells, immune cells, osteoclasts, neurons, and fibroblasts.

Vaccinia virus and other poxviridae are unique among DNA viruses as they replicate only in the cytoplasm of the host cell. Therefore, the large genome is required to code for various enzymes and proteins needed for viral DNA replication. During replication, vaccinia produces several infectious forms which differ in their outer membranes: the intracellular mature virion (IMV), the intracellular enveloped virion (IEV), the cell-associated enveloped virion (CEV) and the extracellular enveloped virion (EEV). IMV is the most abundant infectious form and is thought to be responsible for spread between hosts. On the other hand, the CEV is believed to play a role in cell-to-cell spread and the EEV is thought to be important for long range dissemination within the host organism. The above forms are merely illustrative of the forms for the oncolytic vaccinia virus for use in the compositions and methods in this disclosure.

Any oncolytic strain of vaccinia virus may be used as the vaccinia virus component of the combination of the present disclosure. In preferred embodiments, the oncolytic vaccinia virus of the compositions and methods of the present disclosure is a Copenhagen, Western Reserve or Wyeth strain. Other strains can readily be used including, for example, strains circulating in Korea.

The oncolytic vaccinia virus of the present disclosure can be engineered to express a foreign protein such as granulocyte-macrophage colony stimulating factor, or GM-CSF. GM-CSF is a protein secreted by macrophages that stimulates stem cells to produce granulocytes (neutrophils, eosinophils, and basophils) and macrophages. Human GM-CSF is glycosylated at amino acid residues 23 (leucine), 27 (asparagine), and 39 (glutamic acid) (see U.S. Pat. No. 5,073,627, incorporated herein by reference).

The oncolytic vaccinia virus may be engineered to lack one or more functional genes in order to increase the cancer selectivity of the virus. In one aspect, the oncolytic vaccinia virus may be engineered to lack Thymidine kinase (TK) activity. A TK-deficient vaccinia virus requires thymidine triphosphate for DNA synthesis, which leads to preferential replication in dividing cells (particularly cancer cells). In another aspect, the oncolytic vaccinia virus may be engineered to lack vaccinia virus growth factor (VGF). This secreted protein is produced early in the infection process, acting as a mitogen to prime surrounding cells for infection. In another aspect, the oncolytic vaccinia virus may be engineered to lack both VFG and TK activity. In other aspects, the oncolytic vaccinia virus may be engineered to lack one or more genes involved in evading host interferon (IFN) response such as E3L, K3L, B18R, or B8R. In some embodiments, the oncolytic vaccinia virus is a Western Reserve or Wyeth strain and lacks a functional TK gene. In other embodiments, the oncolytic vaccinia virus is a Western Reserve strain lacking a functional B18R and/or B8R gene.

In some embodiments, the oncolytic vaccinia virus lacks a functional TK gene and expresses human GM-CSF. In a preferred embodiment, the oncolytic vaccinia virus is a Wyeth strain oncolytic vaccinia virus that lacks a functional TK gene and expresses human GM-CSF.

In a particularly preferred embodiment, the oncolytic vaccinia virus is JX-594. JX-594 is a replication-competent, recombinant vaccinia virus derived from the New York Board of Health vaccinia strain that was sold commercially as Dryvax® (Wyeth Laboratories) which is now commonly referred to as Wyeth strain vaccinia virus. JX-594 was derived by inserting the genes for human GM-CSF and E. coli B-galactosidase into the thymidine kinase (TK) gene of the virus (under the control of the synthetic early-late and p7.5 promoters, respectively), thereby rendering the TK gene inactive. Inactivation of the TK gene has been shown to decrease the virulence of vaccinia virus and to increase tumor specific replication. JX-594 has demonstrated replication and GM-CSF expression, associated with tumor responses in patients on clinical trials via both intratumoral and intravenous administration at doses up to $1 \times 10^9$ pfu/dose.

In some embodiments, the oncolytic vaccinia virus is SJ103β (also known as vvDD-CDSR). The vvDD-CDSR virus is a replication-selective oncolytic vaccinia virus with double deletions in the TK and Vaccinia Growth Factor (VGF) genes. vvDD-CDSR is derived by inserting Cytosine Deaminase (CD), Human Somatostatin Receptor Type 2 (SSTR2), and gpt into the TK gene of the Western Reserve (WR) strain of Vaccinia Virus (under the control of the synthetic early-late, synthetic late, and p7.5 promoters, repectively). E. coli β-galactosidase is inserted with homologous recombination into the VGF gene. Inactivation of both the TK and VGF gene has been shown to decrease the virulence of vaccinia virus for safety as well as to enhance tumour specific replication for selectivity. Inactivation of either or both may be achieved by such insertions, by inactivating mutations and/or by partial or complete deletion of the gene. In some embodiments, the oncolytic vaccinia virus is vvDD. vvDD is a replication-selective oncolytic vaccinia virus with double disruptions of the TK and VGF genes of the parental WR strain. Inactivation of both genes increases tumour specificity for viral replication and attenuates the virus for safety. In some embodiments, the oncolytic vaccinia virus is SJ-102. SJ-102 is a replication-competent, recombinant vaccinia virus derived from the Wyeth-calf adapted New York City Department of Health Laboratories strain. The parental vaccinia virus Wyeth strain was engineered by inserting gpt and green fluorescent protein (GFP) at the TK locus to produce the SJ-102 virus. gpt is a selection marker, controlled under the p7.5 early-late viral promoter and confers resistance to an inhibitor of the enzyme inosine monophosphate dehydrogenase. GFP is another visual selection marker and is controlled under a synthetic early-late promoter pSE/L. In some embodiments, the oncolytic vaccinia virus is SJ-103. The parental vaccinia virus for the recombinant virus SJ-103 is Western Reserve (WR) strain. Western Reserve strain is derived from Wyeth strain by passaging in mice in order to enhance tumour selectivity in a mouse cell line and increase the oncolytic effect in vitro. The thymidine Kinase (TK) gene of WR strain is disrupted by inserting gpt and green fluorescent protein (GFP) to produce the SJ-103 virus. gpt is controlled under the p7.5 early-late viral promoter and GFP is controlled under a synthetic early-late promoter pSE/L. In some embodiments, the oncolytic vaccinia virus is WR TK(−). The parental vaccinia virus for the recombinant virus WR TK(−) is Western Reserve (WR) strain. The thymidine kinase gene of WR strain has been disrupted in WR TK(−) by inserting a selection marker. In some embodiments, the oncolytic vaccinia virus is a Lister strain variant from the Institute of Viral Preparations (LIVP). In some embodiments, the oncolytic vaccinia virus is GL-ONC1 (Genelux), also known as GLV-lh68 or RVGL21. GL-ONC1 is a genetically-engineered attenuated LIVP strain vaccinia virus carrying transgenes encoding *Renilla* luciferase, green fluorescent protein (both inserted at the F14.5L locus), β-galactosidase (inserted at the J2R locus, which encodes thymidine kinase), and B-glucuronidase (inserted at the A56R locus, which encodes hemagglutinin). In some embodiments, the oncolytic vaccinia virus is WR ΔB18R luc+. WR ΔB18R luc+ is the WR vaccinia virus with the B18R gene deleted and a luciferase gene inserted to the TK gene.

Vaccinia virus may be propagated using the methods described by Earl and Moss (Ausubel et al. (1994) *Current Protocols in Molecular Biology*, pages 16.15.1 to 16.18.10) or the methods described in WIPO Publication No. WO2013/022764, both of which are incorporated herein by reference.

B. Other Poxviruses

The genus Orthopoxvirus is relatively more homogeneous than other members of the Chordopoxvirinae subfamily and includes 11 distinct but closely related species, which includes vaccinia virus, variola virus (causative agent of smallpox), cowpox virus, buffalopox virus, monkeypox virus, mousepox virus and horsepox virus species as well as others (see Moss, (1996) *Fields Virology*, 3:3637-2672). Certain embodiments of the present disclosure, as described herein, may be extended to other members of Orthopoxvirus genus as well as the Parapoxvirus, Avipoxvirus, Capripoxvirus, Leporipoxvirus, Suipoxvirus, Molluscipoxvirus, and Yatapoxvirus genus. A genus of poxvirus family is generally defined by serological means including neutralization and cross-reactivity in laboratory animals. Various members of the Orthopoxvirus genus, as well as other members of the Chordovirinae subfamily utilize immunomodulatory molecules, examples of which are provided herein, to counteract the immune responses of a host organism. Thus, the present disclosure described herein is not limited to vaccinia virus, but may be applicable to a number of viruses.

Myxomavirus

In one embodiment, the oncolytic virus for use in the compositions and methods of this disclosure is Myxoma virus. Myxoma Virus ("MV") is the causative agent of myxomatosis in rabbits. MV belongs to the Leporipoxvirus genus of the Poxviridae family, the largest of the DNA viruses. MV induces a benign disease in its natural host, the *Sylvilagus* rabbit in the Americas. However, it is a virulent and host-specific poxvirus that causes a fatal disease in European rabbits, characterized by lesions found systemically and especially around the mucosal areas. (Cameron C, Hota-Mitchell S, Chen L, Barrett J, Cao J X, Macaulay C, Wilier D, Evans D, McFadden G. Virology 1999, 264(2): 298-318; Kerr P & McFadden G. Viral Immunology 2002, 15(2): 229-246).

MV is a large virus with a double-stranded DNA genome of 163 kb which replicates in the cytoplasm of infected cells (B. N. Fields, D. M. Knipe, P. M. Howley, Eds., Virology Lippincott Raven Press, New York, 2nd ed., 1996). MV is known to encode a variety of cell-associated and secreted proteins that have been implicated in down-regulation of the host's immune and inflammatory responses and inhibition of apoptosis of virus-infected cells. MV can be taken up by all human somatic cells. MV can infect and kill cancer cells, including human tumour cells.

The Myxoma virus may be any virus that belongs to the Leporipoxvirus species of pox viruses that is replication-competent. The Myxoma virus may be a wild-type strain of Myxoma virus or it may be a genetically modified strain of Myxoma virus.

The Myxoma virus genome may be readily modified to express one or more therapeutic transgenes using standard molecular biology techniques known to a skilled person, and described for example in Sambrook et al. ((2001) Molecular Cloning: a Laboratory Manual, 3rd ed., Cold Spring Harbour Laboratory Press). A skilled person will be able to readily determine which portions of the Myxoma viral genome can be deleted such that the virus is still capable of productive infection. For example, non-essential regions of the viral genome that can be deleted can be deduced from comparing the published viral genome sequence with the genomes of other well-characterized viruses (see for example C. Cameron, S. Hota-Mitchell, L. Chen, J. Barrett, J.-X. Cao, C. Macaulay, D. Willer, D. Evans, and G. McFadden, Virology (1999) 264: 298-318)).

In some embodiments, the oncolytic Myxoma virus is vMyxlac: a recombinant Lausanne strain containing the *E. coli* lacZ gene inserted at an innocuous site between open reading frames M010L and M011L. In some embodiments, the oncolytic Myxoma virus is vMyxT5KO, a recombinant virus with copies of the M-T5 gene replaced by lacZ. In some embodiments, the oncolytic Myxoma virus is SG33, also known as CNCM 1-1594. SG33 virus contains a deletion of about 15 kb in the right-hand portion of its genome. Compared to a reference Lausanne strain, the genes M151R and M001R are only partially deleted, producing inactive truncated proteins. The genes M152R, M153R, M154L, M156R, as well as the genes for the right-hand ITR M008.1R, M008R, M007R, M006R, M005R, M004.1R, M004R, 114003.2R, M003.1R, and M002R are completely deleted. Another alteration between the genome of the SG33 strain and that of the reference Lausanne strain is at the level of the M011L gene (positions 14125-13628 in the genome of the Lausanne strain), encoding an inhibitor of apoptosis (M11L, GenBank NP_051725). It is possible to use a modified attenuated Myxoma virus expressing a desired gene (for example a therapeutic gene of the herpesvirus Thymidine kinase type or FCU, produced from the fusion between the genes encoding Cytosine deaminase and Uracil phosphoribosyltransferase) (ERRS et al, *Cancer Gene therapy*, 15, 18-28, 2008). Attenuated Myxoma viruses modified to express a gene of interest are described in FR2736358.

Parapoxvirus

In one embodiment, the oncolytic virus for use in the compositions and methods of this disclosure is Parapoxvirus. Parapoxvirus orf virus is a poxvirus that induces acute cutaneous lesions in different mammalian species, including humans. Parapoxvirus orf virus naturally infects sheep, goats and humans through broken or damaged skin, replicates in regenerating epidermal cells and induces pustular leasions that turn to scabs. The parapoxvirus orf virus encodes the gene OV20.0L that is involved in blocking PKR activity. The parapoxvirus orf virus is unable to replicate in cells that do not have an activated Ras-pathway. A more preferred oncolytic virus is an "attenuated parapoxvirus orf virus" or "modified parapoxvirus orf virus," in which the gene product or products which prevent the activation of PKR are lacking, inhibited or mutated such that PKR activation is not blocked. Preferably, the gene OV20.0L is not transcribed. Such attenuated or modified parapoxvirus orf virus would not be able to replicate in normal cells that do not have an activated Ras-pathway, but it is able to infect and replicate in cells having an activated Ras-pathway.

In some embodiments, the oncolytic Parapoxvirus is an orf virus strain selected from OV NZ-2 (New Zealand-2), OV NZ-7 (New Zealand-7), and OV-SA00. In some embodiments, the oncolytic Parapoxvirus is a recombinant orf virus (ORFV) containing one or more heterologous host range genes, wherein said genes allow for replication of the virus in human cells. The heterologous host range genes can include, without limitation, SPI-1, SPI-2, KIL, C7L, p28/N1R, B5R, E3L, K3L, M-T2, M-T4, M-T5, M11L, M13L, M063, and F11L.

C. Herpesviruses

Herpes Simplex Virus

In one aspect, the disclosure provides a composition containing an oncolytic virus and a biocompatible microparticle or hydrophilic polymer gel suitable for active embolization. In one embodiment, the oncolytic virus is a Herpesviridae virus, such as herpes simplex virus-1 (HSV-1) or herpes simplex virus-2 (HSV-2). Human herpesviridae viruses include herpes simplex virus-1 ("HSV-1"), herpes simplex virus-2 ("HSV-2"), human cytomegalovirus ("HCMV"), Epstein-Barr virus ("EBV"), Kaposi's sarcoma ("HHV-8"), roseolovirus-6A ("HHV-6A"), and roseolovirus-6B ("HHV-6B").

The HSV virion is a large (120 to 300 nm in diameter), enveloped virus with an icosahedral capsid. It has double stranded DNA with a genome that encodes at least 70 polypeptides. This large amount of regulatory information permits the virus to control its own gene expression and to modify multiple complex events within the infected cell. The herpes simplex virus enters the host by direct contact, is spread to a target tissue only, spreads within the host via neuronal axonal flow, targets the dorsal root ganglia and after recovery of the host from an acute infection, remains latent in the targeted tissue. The limited spread makes HSV a good candidate for an oncolytic virus.

In HSV, mutations allowing selective oncolytic activity include mutation to the genes encoding ICP34.5, ICP6 and/or thymidine kinase (TK), preferably ICP34.5. Such mutations to the ICP34.5-encoding gene in laboratory strains of HSV are described in Chou et al 1990, Maclean et al 1991, although any mutation in which ICP34.5 is non-functional may be used. Accordingly, in an HSV strain, the viruses preferably modified such that it lacks one or more of a functional ICP34.5-encoding gene, a functional ICP6-encoding gene, a functional glycoprotein H-encoding gene, a functional thymidine kinase-encoding gene; or in a non-HSV strain, the virus lacks a functional gene equivalent to one of said HSV genes. More preferably, the virus lacks a functional ICP34.5-encoding gene. Other modifications may also be made. In particular, the HSV virus may be modified such that it lacks a functional ICP47 gene. This is because ICP47 usually functions to block antigen presentation in HSV-infected cells so its disruption leads to a virus that does not confer on infected tumor cells particular properties that might protect such HSV infected cells from the host's immune system. Further, the HSV virus may be modified to express the human GM-CSF gene. Secreted or otherwise released GM-CSF can attract dendritic cells to the tumor enhancing the immune response against the tumor cells.

When the virus of the invention is a herpes simplex virus, the virus may be derived from, for example HSV1 or HSV2 strains, or derivatives thereof, preferably HSV1. A preferred HSV-1 strain is JS-1, which can be modified by inactivation of the ICP34.5 and ICP47 genes and addition of the human GM-CSF (e.g., Senzer et al. *JCO* (2009) 27(34): 5763-5771). In some embodiments, wild-type HSV-1 is obtained from ATCC (VR-735) and no engineering is performed. In some embodiments, the HSV-1 strain is MP (mutant strain of Herpes Simplex Virus type 1). In some embodiments, the HSV-1 virus is Talimogene laherparepvec, also known as OncoVEX GMCSF or T-VEC (AMGEN). T-VEC was produced by modification of the HSV-1 JS-1 parent strain to attenuate the virus and increase selectively for cancer cells. The JS-1 strain was modified via deletion of the ICP34.5 and ICP47 genes (to prevent infection of non-tumor cells and enables antigen presentation, respectively), earlier insertion of the US11 gene (to increase replication and oncolytic ability), and insertion of the human GM-CSF gene (to increase the anti-tumor immune response). In some embodiments, the oncolytic HSV-1 virus is HSV1716, also known as SEPREHVIR. The HSV1716 strain contains a deletion of the ICP34.5 gene, allowing for selective replication in tumor cells. In some embodiments, the HSV-1 virus is HSV1716NTR, an oncolytic virus generated by inserting the enzyme nitroreductase (NTR) into the virus HSV1716 as a gene-directed enzyme prodrug therapy (GDEPT) strategy. In some embodiments, the HSV-1 virus is G207, an oncolytic virus derived by deletion of the ICP34.5 gene and inactivation of the ICP6 gene by insertion of the *E. coli* LacZ gene into a parent HSV-1 laboratory strain F. In some embodiments, the HSV-1 virus is NV1020, an oncolytic virus derived by deletion of one copy of the ICP34.5 gene.

Derivatives include inter-type recombinants containing DNA from HSV1 and HSV2 strains. Such inter-type recombinants are described in the art, for example in Thompson et al (1998) and Meignier et al (1988). A derivative may have the sequence of a HSV1 or HSV2 genome modified by nucleotide substitutions, for example from 1, 2 or 3 to 10, 25, 50 or 100 substitutions. The HSV1 or HSV2 genome may alternatively or additionally be modified by one or more insertions and/or deletions and/or by an extension at either or both ends.

Cytomegalovirus

In one embodiment, the oncolytic virus for use in the compositions and methods of the disclosure is Cytomegalovirus. Cytomegalovirus (CMV), also known as human herpesvirus 5 (HHV-5), is a herpes virus classified as being a member of the beta subfamily of herpesviridae. According to the Centers for Disease Control and Prevention, CMV infection is found fairly ubiquitously in the human population, with an estimated 40-80% of the United States adult population having been infected. The virus is spread primarily through bodily fluids and is frequently passed from pregnant mothers to the fetus or newborn. In most individuals, CMV infection is latent, although virus activation can result in high fever, chills, fatigue, headaches, nausea, and splenomegaly.

Although most human CMV infections are asymptomatic, CMV infections in immunocompromised individuals, (such as HIV-positive patients, allogeneic transplant patients and cancer patients) or persons whose immune system has yet fully developed (such as newborns) can be particularly problematic (Mocarski et al., Cytomegalovirus, in Field Virology, 2701-2772, Editor: Knipes and Howley, 2007). CMV infection in such individuals can cause severe morbidity, including pneumonia, hepatitis, encephalitis, colitis, uveitis, retinitis, blindness, and neuropathy, among other deleterious conditions. In addition, CMV infection during pregnancy is a leading cause of birth defects (Adler, 2008 J. Clin Virol, 41:231; Arvin et al, 2004 Clin Infect Dis, 39:233; Revello et al, 2008 J Med Virol, 80:1415). CMV infects various cells in vivo, including monocytes, macrophages, dendritic cells, neutrophils, endothelial cells, epithelial cells, fibroblasts, neurons, smooth muscle cells, hepatocytes, and stromal cells (Plachter et al. 1996, Adv. Virus Res. 46:195). Although clinical CMV isolates replicate in a variety of cell types, laboratory strains AD169 (Elek & Stem, 1974, Lancet 1:1) and Towne (Plotkin et al., 1975, Infect. Immun. 12:521) replicate almost exclusively in fibroblasts (Hahn et al., 2004, J. Virol. 78:10023). The restriction in tropism, which results from serial passages and eventual adaptation of the virus in fibroblasts, is stipulated a marker of attenuation (Gerna et al., 2005, J. Gen. Virol. 86:275; Gerna et al, 2002, J. Gen Virol. 83:1993; Gerna et al, 2003, J. Gen Virol. 84:1431; Dargan et al, 2010, J. Gen Virol. 91:1535). Mutations causing the loss of epithelial cell, endothelial cell, leukocyte, and dendritic cell tropism in human CMV laboratory strains have been mapped to three open reading frames (ORFs): UL128, UL130, and UL131 (Hahn et al., 2004, J. Virol. 78:10023; Wang and Shenk, 2005 J. Virol. 79:10330; Wang and Shenk, 2005 Proc Natl Acad Sci USA. 102:18153). Biochemical and reconstitution studies show that UL128, UL130 and UL131 assemble onto a gH/gL scaffold to form a pentameric gH complex (Wang and Shenk, 2005 Proc Natl Acad Sci USA. 102:1815; Ryckman et al, 2008 J. Virol. 82:60). Restoration of this complex in virions restores the viral epithelial tropism in the laboratory strains (Wang and Shenk, 2005 J. Virol. 79:10330). Loss of endothelial and epithelial tropism has been suspected as a deficiency in the previously evaluated as vaccines such as Towne (Gerna et al, 2002, J. Gen Virol. 83:1993; Gerna et al, 2003, J. Gen Virol. 84:1431). Neutralizing antibodies in sera from human subjects of natural CMV infection have more than 15-fold higher activity against viral epithelial entry than against fibroblast entry (Cui et al, 2008 Vaccine 26:5760). Humans with primary infection rapidly develop neutralizing antibodies to viral endothelial and epithelial entry but only slowly develop neutralizing antibodies to viral fibroblast entry (Gerna et al, 2008 J. Gen. Virol. 89:853). Furthermore, neutralizing activity against viral epithelial and endothelial entry is absent in the immune sera from human subjects who received Towne vaccine (Cui et al, 2008 Vaccine 26:5760). More recently, a panel of human monoclonal antibodies from four donors with HCMV infection was described, and the more potent neutralizing clones from the panel recognized the antigens of the pentameric gH complex (Macagno et al, 2010 J. Virol. 84:1005).

D. Measles Virus

In one embodiment, the oncolytic virus for use in the compositions and methods of this disclosure is Measles virus. Measles virions are large and pleitrophic with diameters of up to ~550 nm. Measles virus is a negative strand RNA virus whose genome encodes six protein products, the N (nucleocapsid), P (polymerase cofactor phosphoprotein), M (matrix), F (fusion), H (hemaglutinin) and L (large RNA polymerase) proteins. The H protein is a surface glycoprotein which mediates measles virus attachment to its receptor, CD46 (Dorig, et al., Cell 75: 295-305, 1993). The F protein is responsible for cell-cell fusion after viral attachment has taken place. Measles virus has a natural tropism for lymphoid cells and, in particular, cancerous lymphoid cells.

The tumor selectivity of the virus is due to intracellular restrictions to the life cycle of the virus that is strongly inhibitory to virus propagation in nontransformed cells, but which are overriden by cellular factors present in neoplastic cells (Robbins, et al., Virology 106: 317-326, 1980; Robbins, Intervirology 32: 204-208, 1991). Measles infectivity of lymphoid cells causes a very characteristic cytopathic effect. Multinucleated giant cells develop during measles virus replication in lymph nodes as a result of gross cell-cell fusion (Warthin, Arch. Pathol. 11: 864-874, 1931). In tissue culture, infection with measles virus can cause fusion of a whole monolayer of cells. The F and H antigens are found on the surface of infected cells. Thus, cells which are infected by measles virus and whose membranes express F and H proteins become highly fusogenic and can cause fusion not only of other infected cells but also of neighboring cells which are not infected (Norrby and Oxman, "Measles Virus." In Virology, 1990, B. N. Fields, et al., eds. New York, Raven Press, Ltd., pp 1013-1044). The expression of viral antigens on the surface of a tumor cell can also mediate a tumor specific immune response.

An attenuated strain of virus can be obtained by serial passage of the virus in cell culture (e.g., in non-human cells), until a virus is identified which immunogenic but not pathogenic. While wild type virus will cause fatal infection in marmosets, vaccine strains do not. In humans, infection with wild type viral strains is not generally fatal but is associated with classic measles disease. Classic measles disease includes a latent period of 10-14 days, followed by a syndrome of fever, coryza, cough, and conjunctivitis, followed by the appearance of a maculopapular rash and Koplik's spots (small, red, irregularly shaped spots with blue-white centers found inside the mouth). The onset of the rash coincides with the appearance of an immune response and the initiation of virus clearance. In contrast, individuals receiving an attenuated measles virus vaccine do not display classical measles symptoms. Attenuation is associated with decreased viral replication (as measured in vivo by inability to cause measles in monkeys), diminished viremia, and failure to induce cytopathological effects in tissues (e.g., cell-cell fusion, multinucleated cells). However, these biological changes have not been mapped to any single genetic change in the virus genome.

An attenuated strain of measles virus which has been clinically tested as a vaccine for measles infection is used to provide an effective dose which will limit and/or cause regression of a group of cancer cells, such as a tumor. The Moraten attenuated form of the virus has been used worldwide as a vaccine and has an excellent safety record (Hilleman, et al., J. Am. Med. Assoc. 206: 587-590, 1968). Accordingly, in one embodiment of the invention, the Moraten strain is used to provide an effective dose. The Moraten vaccine is commercially available from Merck® and is provided lyophilized in a vial which when reconstituted to 0.5 ml comprises 103 pfu/ml. A vaccine against the Moraten Berna strain is available from the Swiss Serum Vaccine Institute Berne.

In a further embodiment of the invention, the Edmonston-B vaccine strain of measles virus is used (MV-Edm) (Enders and Peebles, Proc. Soc. Exp. Biol. Med. 86: 277-286, 1954). MV-Edm grows efficiently in tumor cells but its growth is severely restricted in primary cultures of human peripheral blood mononuclear cells, normal dermal fibroblasts, and vascular smooth muscle cells. A form of the Enders attenuated Edmonston strain is available commercially from Merck (Attenuvax®). In some embodiments, the measles virus is MV-NIS. MV-NIS is a measles virus encoding the human thyroidal sodium iodide symporter (MV-NIS). The measles virus for MV-NIS is an attenuated oncolytic Edmonston (ED) strain. MV-NIS is selectively destructive to myeloma plasma cells and MV-NIS infected cells can be imaged via uptake of iodine 123 (I-123).

Other attenuated measles virus strains are also encompassed within the scope of the invention, such as Leningrad-16, and Moscow-5 strains (Sinitsyna, et al., Res. Virol. 141(5): 517-31, 1990), Schwarz strain (Fourrier, et al., Pediatrie 24(1): 97-8, 1969), 9301B strain (Takeda, et al. J.

VIROL. 72/11: 8690-8696), the AIK-C strain (Takehara, et al., Virus Res 26 (2): 167-75, 1992 November), and those described in Schneider-Shaulies, et al., PNAS 92(2): 3943-7, 1995, the entireties of which are incorporated by reference herein.

In a further embodiment of the invention, the measles virus is provided in a composition comprising a mixture of attenuated oncolytic viruses. In one embodiment, the mumps measles and rubella vaccine (MMR) is used. The MMR vaccine was introduced into the United States in 1972 and into the United Kingdom in 1998. Commercially available preparations of the MMR vaccine is obtainable from Merck, Pasterur Merieux Connaught, or SmithKline Beecham, and also contain the Moraten strain of attenuated measles virus at a minimum titer of 1 PFU/ml. In still a further embodiment of the invention, the measles virus is provided in a composition comprising Edmonston Zagreb measles strain (an attenuated strain obtained from the Edmonston-enders stain) and the Wistar RA 27/3 strain of rubella (Swiss Serum Vaccine Institute Berne). It should be apparent to those of skill in the art that any clinically tested measles vaccine is acceptable for use in the invention, and is encompassed within the scope of the invention.

In still a further embodiment of the invention, recombinant measles viruses comprising genetic modifications are derived from wild type measles virus to generate attenuated viruses, e.g., viruses having high immunogenicity (as measured by 70-100% seroconversion) and no pathogenicity (e.g., not producing classical measles symptoms, as discussed above). In one embodiment of the invention, genetic modifications are introduced through random mutagenesis of a plasmid comprising the sequence of a wild type measles virus. Sequences of wild type isolates are disclosed in U.S. Pat. No. 5,578,448, the entirety of which is enclosed herein by reference.

In another embodiment of the invention, particular cistrons in the measles virus genome are targeted to modify genes whose expression is associated with attenuation (Schneider-Shaulies, et al. PNAS 92(2): 3943-7, 1995; Takeda, et al. J. Virol. 1998 72/11 (8690-8696)). Thus, in one embodiment of the invention, a recombinant measles virus strain is generated comprising a single point mutation or multiple non-contiguous point mutations in any of an H protein, a V protein, a C protein, and combinations thereof. In still a further embodiment of the invention, natural variants of the wild type or attenuated measles viruses are identified (e.g., such as from cultures of virus from infected patients) which have at least one point mutation in their genome.

Engineering of the Oncolytic Virus

In certain embodiments, the oncolytic viruses for use in the compositions and methods of this disclosure may be engineered to improve the efficacy, safety or other characteristic of the virus. Viruses are frequently inactivated, inhibited or cleared by immunomodulatory molecules such as interferons (-α, -β, -γ) and tumor necrosis factor-α (TNF) (Moss, 1996). Inactivation may be achieved by inactivation of a viral gene, which may be achieved by insertion(s) into the gene, by inactivating mutations in the gene and/or by partial or complete deletion of the gene. Host tissues and inflammatory/immune cells frequently secrete these molecules in response to viral infection. These molecules can have direct antiviral effects and/or indirect effects through recruitment and/or activation of inflammatory cells and lymphocytes. Given the importance of these immunologic clearance mechanisms, viruses have evolved to express gene products that inhibit the induction and/or function of these cytokines/chemokines and interferons. For example, vaccinia virus (VV; and some other poxviruses) encodes the secreted protein vCKBP (B29R) that binds and inhibits the CC (two adjacent cysteines) chemokines (e.g., RANTES, eotaxin, MIP-1-alpha) (Alcami et al., 1998). Some VV strains also express a secreted viral protein that binds and inactivates TNF (e.g., Lister A53R) (Alcami et al., 1999). Most poxvirus strains have genes encoding secreted proteins that bind and inhibit the function of interferons-α/β (e.g., B18R) or interferon-γ(B8R). vC12L is an IL-18-binding protein that prevents IL-18 from inducing IFN-γ and NK cell/cytotoxic T-cell activation.

Most poxvirus virulence research has been performed in mice. Many, but not all, of these proteins are active in mice (B18R, for example, is not). In situations in which these proteins are active against the mouse versions of the target cytokine, deletion of these genes leads to reduced virulence and increased safety with VV mutants with deletions of or functional mutations in these genes. In addition, the inflammatory/immune response to and viral clearance of these mutants is often increased compared to the parental virus strain that expresses the inhibitory protein. For example, deletion of the T1/35 kDa family of poxvirus-secreted proteins (chemokine-binding/-inhibitory proteins) can lead to a marked increase in leukocyte infiltration into virus-infected tissues (Graham et al., 1997). Deletion of the vC12L gene in VV leads to reduced viral titers/toxicity following intranasal administration in mice; in addition, NK cell and cytotoxic T-lymphocyte activity is increased together with IFN-γ induction (Smith et al., 2000). Deletion of the Myxoma virus T7 gene (able to bind IFN-γ and a broad range of chemokines) results in reduced virulence and significantly increased tissue inflammation/infiltration in a toxicity model (Upton et al., 1992; Mossman et al., 1996). Deletion of the M-T2 gene from myxoma virus also resulted in reduced virulence in a rabbit model (Upton et al. 1991). Deletion of the B18R anti-interferon-α/β gene product also leads to enhanced viral sensitivity to IFN-mediated clearance, reduced titers in normal tissues and reduced virulence (Symons et al., 1995; Colamonici et al., 1995; Alcami et al., 2000). In summary, these viral gene products function to decrease the antiviral immune response and inflammatory cell infiltration into virus-infected tissues. Loss of protein function through deletion/mutation leads to decreased virulence and/or increased proinflammatory properties of the virus within host tissues. See PCT/US2003/025141, which is hereby incorporated by reference.

Cytokines and chemokines can have potent antitumoral effects (Vicari et al., 2002; Homey et al., 2002). These effects can be on tumor cells themselves directly (e.g., TNF) or they can be indirect through effects on non-cancerous cells. An example of the latter is TNF, which can have antitumoral effects by causing toxicity to tumor-associated blood vessels; this leads to a loss of blood flow to the tumor followed by tumor necrosis. In addition, chemokines can act to recruit (and in some cases activate) immune effector cells such as neutrophils, eosinophils, macrophages and/or lymphocytes. These immune effector cells can cause tumor destruction by a number of mechanisms. These mechanisms include the expression of antitumoral cytokines (e.g., TNF), expression of fas-ligand, expression of perforin and granzyme, recruitment of natural killer cells, etc. The inflammatory response can eventually lead to the induction of systemic tumor-specific immunity. Finally, many of these cytokines (e.g., TNF) or chemokines can act synergistically with chemotherapy or radiation therapy to destroy tumors.

Clinically effective systemic administration of recombinant versions of these immunostimulatory proteins is not feasible due to (1) induction of severe toxicity with systemic administration and (2) local expression within tumor tissue is needed to stimulate local infiltration and antitumoral effects. Approaches are needed to achieve high local concentrations of these molecules within tumor masses while minimizing levels in the systemic circulation. Viruses can be engineered to express cytokine or chemokine genes in an attempt to enhance their efficacy. Expression of these genes from replication-selective vectors has potential advantages over expression from non-replicating vectors. Expression from replicating viruses can result in higher local concentrations within tumor masses; in addition, replicating viruses can help to induce antitumoral immunity through tumor cell destruction/oncolysis and release of tumor antigens in a proinflammatory environment. However, there are several limitations to this approach. Serious safety concerns arise from the potential for release into the environment of a replication-competent virus (albeit tumor-selective) with a gene that can be toxic if expressed in high local concentrations. Viruses that express potent pro-inflammatory genes from their genome may therefore pose safety risks to the treated patient and to the general public. Even with tumor-targeting, replication-selective viruses expressing these genes, gene expression can occur in normal tissues resulting in toxicity. In addition, size limitations prevent expression of multiple and/or large genes from viruses such as adenovirus; these molecules will definitely act more efficaciously in combination. Finally, many of the oncolytic viruses in use express anti-inflammatory proteins and therefore these viruses will counteract the induction of a proinflammatory milieu within the infected tumor mass. The result will be to inhibit induction of antitumoral immunity, antivascular effects and chemotherapy-/radiotherapy-sensitization.

Embolic Agents

Numerous biocompatible microparticle or hydrophilic polymer gel agents can be used the compositions and methods of this disclosure. In a preferred embodiment, the biocompatible microparticle or hydrophilic polymer gel agents are selected from: degradable starch microparticles, polyvinyl alcohol microparticles, gelatin foam microparticles, and sulfonated polyvinyl alcohol hydrogel microparticles. In one aspect the biocompatible microparticle or hydrophilic polymer gel agent increases the viral output from tumor cells cultured in vitro by at least 50%, at least 75%, at least 100%, at least 150%, at least 200% or at least 300%. In a related aspect the biocompatible microparticle or hydrophilic polymer gel agent increases the viral output from tumor cells cultured in vitro by between 50% and 400%, between 75% and 400%, between 100% and 400%, between 150% and 400%, between 200% and 400%, or between 300% and 400%.

Biocompatible microparticle or hydrophilic polymer gel agents ("embolic agents") can be either temporary or permanent. Exemplary temporary embolic agents include gelfoam, collagen, and thrombin. Exemplary permanent embolic agents include particles, such as polyvinyl alcohol particles (PVA) and embospheres, coils, such as pushable, injectable, detachable, mechanical, electrolytic, and hydrolytic coils, liquid agents, such as glue, onyx, alcohol, and ALGEL™ (a hydrogel, sugar-based polymer derived from alginate), and other agents, including amplatzer plugs, Gianturco-Grifka vascular occlusive device (GGVODs), and detachable balloons. Different embolic agents can be used depending on the size of the vessel to be embolized, the desired length of vessel occlusion following embolization, and whether embolized tissue should remain viable after occlusion. Given the extensive use of embolization, a skilled interventional radiologist would have no difficulty in selecting the appropriate type of agent, size range of agent, etc. to achieve the desired embolization. Vessel occlusion is useful in clinical scenarios such as traumatic injury and hemorrhage, or when repeated embolization procedures are desired, such may be desirable as in tumor embolization with oncolytic viruses as disclosed in this specification.

In one embodiment, the biocompatible microparticle or hydrophilic polymer gel agents are gelatin foam microparticles. Exemplary gelatin foam includes Gelfoam, produced by Alicon/Scion Medical Technologies. Gelfoam is a biological substance made from purified skin gelatin, and is formulated in sterile sheets or as a powder. Gelfoam has been used in embolization applications for over 30 years, and is a low cost, versatile embolic agent. Gelfoam slows blood flow by causing mechanical obstruction. Gelfoam powder consists of particulates that range in size from 150-1000 µm and can aggregate to form larger conglomerate particles upon water absorption. Gelfoam sheets can be cut into numerous different sizes and shapes and formulated with other aqueous agents upon injection depending upon the desired application. Gelfoam slurry containing both a contrast agent and Gelfoam sponge can be used to form a "cast" of proximal embolized vessels, while Gelfoam torpedoes or cubes can be used for larger vessels. Gelfoam temporarily occludes vessels by slowing blood flow, increasing thrombus formation, and functioning as a scaffold for clots.

In one embodiment, the biocompatible microparticle or hydrophilic polymer gel agents are degradable starch microparticles. Exemplary degradable starch microparticles (DSM) are EMBOCEPTS particles produced by Pharmacept and SPHEREX particles produced by Mangle Life Sciences. EMBOCEPTS particles (Amilomer as the active substance) are cross-linked particles composed of hydrolyzed potato starch. These particles are suitable for temporary embolization, as they have a half-life of approximately 35 minutes and are degradable. SPHEREX particles are composed of DSM-S microparticles, sterilized and suspended in saline solution. Starch microparticles may be prepared from an aqueous solution of purified amylopectin-based starch of reduced molecular weight by forming an emulsion of starch droplets in an outer phase of polymer solution, converting the starch droplets to a gel, and drying the starch particles. A release-controlling shell is optionally also applied to the particles. Biodegradable microparticles, after parenteral administration, are dissolved in the body to form endogenic substances, ultimately, for example, glucose. The biodegradability can be determined or examined through incubation with a suitable enzyme, for example alpha-amylase, in vitro. The biodegradability can also be examined through parenteral injection of the microparticles, for example subcutaneously or intramuscularly, and histological examination of the tissue as a function of time. Biodegradable starch microparticles disappear normally from the tissue within a few weeks and generally within one week. In those cases in which the starch microparticles are coated with a release-controlling shell, for example coated, it is generally this shell which determines the biodegradability rate, which then, in turn, determines when alpha-amylase becomes available to the starch matrix.

In one embodiment, the biocompatible microparticle or hydrophilic polymer gel agents are polyvinyl alcohol (PVA) microparticles. Exemplary polyvinyl alcohol microparticles are produced by Boston Scientific Corporation (Natick, Mass.). PVA particles are made from a PVA foam sheet that is vacuum dried and scraped into particles. The particles are filtered with sieves and are available in sizes ranging from 100 µm to 1100 µm. Polyvinyl alcohol particles are irregular in size and shape, which promotes aggregation. After suspension, PVA particles can be oblong, oval, irregular, sharp, and angulated with small fragments after suspension. Polyvinyl alcohol particles deliver permanent occlusion by adhering to vessel walls and by blocking the smallest vessel into which they pass. PVA occlusion results in inflammatory reactions, local vessel necrosis, and subsequent vessel fibrosis.

In one embodiment, the biocompatible microparticle or hydrophilic polymer gel agents are sulfonated polyvinyl alcohol hydrogel microparticles. Exemplary sulfonated polyvinyl alcohol hydrogel microparticles are DC-Beads produced by Biocompatibles (UK, Surrey, UK). DC Beads are embolic microparticle products based on a polyvinyl alcohol hydrogel that has been modified with sulfonate groups. DC Beads have the ability to actively sequester anthracycline compounds in their salt form, such as doxorubicin HCl, from solution and release it in a controlled and sustained manner. A drug can be added immediately prior to embolization, allowing for a one-step procedure in which the drug and device are delivered at the same time, resulting in a sustained local delivery of the drug.

As mentioned above, one of skill in the art can readily select the appropriate size of the biocompatible microparticle or hydrophilic polymer gel agents based upon, amontg other factors, the size of the tumor vasculature and the nature of the desired embolization. In a preferred embodiment, the biocompatible microparticle or hydrophilic polymer gel agents are between 100 µm and 2000 µm in size. In a preferred embodiment, the biocompatible microparticle or hydrophilic polymer gel agents are between 150 and 350 µm in size. In one embodiment, the biocompatible microparticle or hydrophilic polymer gel agents are between 150 and 200 µm in size. In one embodiment, the biocompatible microparticle or hydrophilic polymer gel agents are between 200 and 250 µm in size. In one embodiment, the biocompatible microparticle or hydrophilic polymer gel agents are between 250 and 300 µm in size. In one embodiment, the biocompatible microparticle or hydrophilic polymer gel agents are between 300 and 350 µm in size.

In certain embodiments, the biocompatible microparticle or hydrophilic polymer gel agents are uniform in size. This means that the difference in diameter between individual particles is from about 0 µm to about 100 µm, from about 0 µm to about 50 µm, or from about 0 µm to about 25 µm. In some embodiments, the microparticles have differences in diameter of 100 µm or less, about 50 µm or less, about 25 µm or less, about 10 µm or less or about 5 µm or less.

Methods of Embolization

In one aspect, the disclosure provides a method for active embolization of a vascular site in a mammal by introducing into the vasculature of a mammal an oncolytic virus of the disclosure and a biocompatible microparticle or hydrophilic polymer gel suitable for active embolization. In one aspect, the disclosure provides a method for active embolization of a vascular site in a mammal by introducing into the vasculature of a mammal an oncolytic virus at least 0.1 um in diameter along the shortest axis and a biocompatible microparticle or hydrophilic polymer gel suitable for active embolization. In one aspect, the disclosure provides a method for active embolization of a vascular site in a mammal by introducing into the vasculature of a mammal an oncolytic virus that buds from an apical surface of an infected polarized cell and a biocompatible microparticle or hydrophilic polymer gel suitable for active embolization. In another aspect, the disclosure provides for a method for treating cancer by debulking a tumor mass, comprising introducing into the vasculature of a mammal an oncolytic virus and a biocompatible microsphere or hydrophilic polymer gel agent suitable for active embolization. Again, viral replication and transient vascular shut down subsequently result in tumor necrosis, thereby 'debulking' the tumor mass without observable damage to the surrounding healthy tissue. In preferred embodiments, the method of debulking results in necrosis of at least 75%, at least 80%, at least 85%, at least 90%, or at least 85% of the embolized tumor mass.

Introduction of the biocompatible microparticle or hydrophilic polymer gel agents, the oncolytic viruses and the compositions of the present disclosure typically carried out by injection into blood vessels near and around tumors. In certain embodiments, the biocompatible microparticle or hydrophilic polymer gel agents, the oncolytic viruses and the compositions of the present disclosure are introduced by a catheter. In other embodiments, the biocompatible microparticle or hydrophilic polymer gel agents, the oncolytic viruses and the compositions of the present disclosure are introduced through injection by a catheter attached to a syringe. In some embodiments, introduction is into a blood vessel that directly feeds a tumor or portion of a tumor. In other embodiments, introduction is directly to the site of action, for example into a blood vessel at the proximal end of the tumor. The biocompatible microparticle or hydrophilic polymer gel agent according to the present disclosure can be introduced already loaded with the oncolytic virus (i.e., the compositions of the present disclosure). In other embodiments, the biocompatible microparticle or hydrophilic polymer gel agents are introduced in combination with the oncolytic virus, wherein the virus is introduced prior, simultaneously or after the introduction of the biocompatible microparticle or hydrophilic polymer gel agents. When introduced, the biocompatible microparticle or hydrophilic polymer gel agents, the oncolytic viruses and the compositions of the present disclosure are suitable for injection. In specific embodiments, the biocompatible microparticle or hydrophilic polymer gel agents, the oncolytic viruses and the compositions of the present disclosure are sterile.

The biocompatible microparticle or hydrophilic polymer gel agents, the oncolytic viruses and the compositions of the present disclosure may be delivered using a catheter or microcatheter. The catheter delivering the biocompatible microparticle or hydrophilic polymer gel agents, the oncolytic viruses and the compositions of the present disclosure may be a small diameter medical catheter. Catheter materials compatible with the biocompatible microparticle or hydrophilic polymer gel agents, the oncolytic viruses and the compositions of the present disclosure may include polyethylene, fluoropolymers and silicone. Once a catheter is in place, the biocompatible microparticle or hydrophilic polymer gel agents, the oncolytic viruses and/or the compositions of the present disclosure are introduced through the catheters slowly, typically with the assistance of fluoroscopic guidance. The biocompatible microparticle or hydrophilic polymer gel agents, the oncolytic viruses and the compositions of the present disclosure may be introduced directly into critical blood vessels or they may be introduced upstream of target vessels. The amount of the biocompatible microparticle or hydrophilic polymer gel agents or the compositions of the present disclosure introduced during an embolization procedure will be an amount sufficient to cause embolization, e.g., to reduce or stop blood flow through the target vessels. The amount of the biocompatible microparticle or hydrophilic polymer gel agents, the oncolytic viruses and the compositions of the present disclosure delivered can vary depending on, e.g., the total size or area of the vasculature to be embolized and the size and nature of the tumor. After embolization, another arteriogram may be performed to confirm the completion of the procedure. Arterial flow will still be present to some extent to healthy body tissue proximal to the embolization, while flow to the diseased or targeted tissue is blocked. Further, a vasodilator (e.g., adenosine) may be administered to the patient beforehand, simultaneously, or subsequently, to facilitate the procedure.

One of skill in the medical or embolizing art will understand and appreciate how the biocompatible microparticle or hydrophilic polymer gel agents, the oncolytic viruses and the compositions of the present disclosure as described herein can be used in various embolization processes by guiding a delivery mechanism to a desired vascular body site, and delivering an amount of the biocompatible microparticle or hydrophilic polymer gel agents, the oncolytic viruses or the compositions of the present disclosure to the site, to cause restriction, occlusion, filling, or plugging of one or more desired vessels and reduction or stoppage of blood flow through the vessels. Factors that might be considered, controlled, or adjusted for, in applying the process to any particular embolization process might include the chosen biocompatible microparticle or hydrophilic polymer gel agent, oncolytic virus and/or composition of the present disclosure (e.g., to account for imaging, tracking, and detection of a radiopaque particle substrate); the biocompatible microparticle or hydrophilic polymer gel agents, the oncolytic viruses and the compositions of the present disclosure delivered to the body site; the method of delivery, including the particular equipment (e.g., catheter) used and the method and route used to place the dispensing end of the catheter at the desired body site, etc. Each of these factors will be appreciated by one of ordinary skill, and can be readily dealt with to apply the described methods to innumerable embolization processes.

In one embodiment, primary and metastatic liver tumors may be treated utilizing embolization therapy of the present disclosure. The liver tumor may be a primary or a secondary tumor. The secondary tumor may be, for example, a metastasized malignant melanoma tumor. Briefly, a catheter is preferably inserted via the femoral artery and advanced into the hepatic artery by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by introducing the biocompatible microparticle or hydrophilic polymer gel agents, the oncolytic viruses and the compositions of the present disclosure through the arterial catheter until flow in the artery to be blocked ceases. Occlusion of the artery may be confirmed by injecting radiopaque contrast through the catheter and demonstrating, preferably by fluoroscopy, that the vessel which previously filled with contrast no longer does so. The same procedure may be repeated with each feeding artery to be occluded.

Combination Therapy

In some embodiments, an additional therapeutic agent is used in combination with Transcatheter Arterial Viroembolization ("TAVE") methods of the present disclosure. Additional therapeutic agents include, without limitation, tyrosine kinsase inhibitors (sunitinib, sorafenib), radiation therapy, and traditional chemotherapeutics. Additional therapeutic agents can be administered following TAVE, for example 2-3 weeks after TAVE. In some embodiments, TAVE is preceeded by administration of an additional therapeutic agent. In some embodiments, TAVE is followed by administration of an additional therapeutic agent. In some embodiments, TAVE occurs simultaneously with administration of an additional therapeutic agent. In some embodiments sequential administration of TAVE and an additional therapeutic agent is repeated in multiple cycles.

Visualization Methods

In some embodiments, a contrast agent is used to visualize the vasculature prior to performing active embolization. Contrast agent visualization enables guidance and monitoring of catheter pacement within the vasculature, allowing active embolization within the desired blood vessel(s). The contrast agent can be tracked and monitored by known methods, including radiography and fluoroscopy. The contrast agent can be any material capable of enhancing contrast in a desired imaging modality (e.g., magnetic resonance, X-ray (e.g., CT), ultrasound, magnetotomography, electrical impedance imaging, light imaging (e.g. confocal microscopy and fluorescence imaging) and nuclear imaging (e.g. scintigraphy, SPECT and PET)). Contrast agents are well known in the arts of embolization and similar medical practices, with any of a variety of such contrast agents being suitable for use in the formulation and methods of the present disclosure.

In some embodiments, the constrast agent is radiopaque; in particular, a radiopaque material which exhibits permanent radiopacity, e.g., a metal or metal oxide. Permanent radiopacity is unlike some other contrast-enhancing agents or radiopaque materials used in embolization or similar medical applications which biodegrade or otherwise lose their effectiveness (radiopacity) over a certain period, e.g., days or weeks, such as 7 to 14 days. (See, e.g., PCT/GB98/02621). Permanent radiopaque materials are often preferable because they can be monitored or tracked for as long as they remain in the body, whereas other non-permanent contrast-enhancing agents or radiopaque materials have a limited time during which they may be detected and tracked.

Radiopaque materials include paramagnetic materials (e.g., persistent free radicals or more preferably compounds, salts, and complexes of paramagnetic metal species, for example transition metal or lanthanide ions); heavy atom (i.e., atomic number of 37 or more) compounds, salts, or complexes (e.g., heavy metal compounds, iodinated compounds, etc.); radionuclide-containing compounds, salts, or complexes (e.g., salts, compounds or complexes of radioactive metal isotopes or radiodinated organic compounds); and superparamagentic particles (e.g., metal oxide or mixed oxide particles, particularly iron oxides). Preferred paramagnetic metals include Gd (III), Dy (III), Fe (II), Fe (III), Mn (III) and Ho (III), and paramagnetic Ni, Co and Eu species. Preferred heavy metals include Pb, Ba, Ag, Au, W, Cu, Bi and lanthanides, such as Gd.

The amount of contrast-enhancing agent used should be sufficient to allow detection of the embolus as desired. Preferably, the embolizing agent composition can comprise from about 1 to about 50 weight percent of contrast agent. The difference in concentration for radiopaque material is as follows: For example, in preferred embodiments, the inverse thermosensitive polymer mixture contains about 50 vol % radiopaque contrast agent solution, wherein preferred contrast agents, e.g., Omnipaque or Visipaque, are non-ionic. For MRI detection, the concentration of the MR detection agent is preferably about 1 weight %.

Examples of suitable contrast agents for use in the present disclosure include, without limitation, metrizamide, iopamidol (Isovue™ or Iopamiron™), iodixanol (Visipaque™) iohexol (Omnipaque™), iopromide (Ultravist™), iobtiridol, iomeprol, iopentol, iopamiron, ioxilan, iotrolan, gadodiamide, gadoteridol, iotrol, ioversol (Optiray™) or combinations thereof.

EXAMPLES

The following are examples of methods and compositions of the present disclosure. It is understood that various other embodiments may be practiced, given the general description provided above.

Example 1: Evaluation of Stability and Viral Replication of JX-594 Vaccinia Virus The stability of JX-594 oncolytic vaccinia virus in combination with other agents used for transarterial chemoembolization (TACE) was evaluated in vitro. JX-594 is a replication-competent, recombinant vaccinia virus derived from Wyeth strain vaccinia virus. JX-594 was derived by inserting the genes for human GM-CSF and E. coli β-galactosidase into the thymidine kinase (TK) gene of the virus (under the control of the synthetic early-late and p7.5 promoters, respectively), thereby rendering the TK gene inactive. Inactivation of the TK gene has been shown to decrease the virulence of vaccinia virus and to increase tumor specific replication.

Methods

JX-594 vaccinia virus was mixed with Lipiodol, Adriamycin, and/or Gelfoam according to the treatment groups summarized in Table 1.

TABLE 1

JX-594 treatment groups and incubation conditions.

| Group | Incubation Conditions |
|---|---|
| 1. JX-594 | 10 min at RT before adding them to the cells |
| 2. JX-594 + Lipiodol | 10 min at RT before adding them to the cells |
| 3. JX-594 + Lipiodol + Adriamycin | 10 min at RT before adding them to the cells |
| 4. Lipiodol + Adriamycin | Pretreatment of the cells 1 h, add JX-594 |
| 5. JX-594 + Gelfoam | 10 min at RT before adding them to the cells |
| 6. Lipiodol + Adriamycin | Pretreatment of the cells 1 h, mix JX-594 + Gelfoam and incubate for 10 min at RT before adding them to the cells |

The mixtures described in the "Group" column of Table 1 were incubated for the indicated time periods before addition to cells (HuH-7 cell line). To prepare viral inoculums, JX-594 purified by sucrose cushion was vortexed vigorously for 30 seconds at full power. Designated amount of JX-594 suspension was diluted in DMEM containing 2.5% fetal bovine serum (infection media). Adriamycin powder (Doxorubicin hydrochloride, SIGMA-ALDRICH®), Lipiodol® (Guerbet), and Gelfoam (Alicon®, Hangzhou Alicon Pharm SCI&TEC Co., Ltd) were dissolved in the same infection media to prepare stock Adriamycin, Lipiodol, and Gelfoam solution. For groups 2, 3, 5, and 6, JX-594 was mixed with Adriamycin, Lipiodol, and/or Gelfoam and incubated for 10 minutes at room temperature before infection. For group numbers 4 and 6, cells were pre-treated with Lipiodol and Adriamycin for 1 hour at room temperature. 200 μL of mixed inoculum was then added into each well of a 24-well tissue culture plate and incubated for 2 hours for viral absorption at 37° C. in humidified CO2 incubator.

Cells were infected at a multiplicity of infection (MOI) of 1 or 100. After 2 hours of viral absorption, cells were washed twice with 500 μL of DMEM containing 2.5% fetal bovine serum. The plates were incubated for 24 or 48 hours at 37° C. in a humidified $CO_2$ incubator. Reagents used for the viral cultures, along with their respective concentrations and sources, are summarized in Table 2. The HuH-7 cells were purchased from JCRB cell bank (Japanese Collection of Research Bioresources, Osaka, Japan) and were cultured in complete growth media (DMEM containing 10% fetal bovine serum). The cells were incubated at 37° C. in a humidified CO2 incubator.

Cell culture supernatant was harvested at 24 and 48 hours post infection, and viral output (pfu/ml) was measured. Infected cells were harvested by scraping using a rubber plunger of a 1 mL syringe. The harvested cell suspension was lysed by three cycles of freezing and thawing. To measure the amount of infectious viral particles, a plaque assay was performed with lysed cell harvest. For the plaque assay, U-2 OS cells were expanded and seeded in 6-well tissue culture plates. The plates were incubated at 37° C. in a humidified $CO_2$ incubator for 16 to 20 hours prior to viral titration. Before infection, lysed HuH-7 cells were serially diluted in serum free DMEM media. 900 μL of DMEM serum free media was added to each well after aspirating complete growth media and 100 μL of each serially diluted inoculum was added. For viral absorption, the plates were incubated at 37° C. in a humidified $CO_2$ incubator for 2 hours. After 2 hours, the inoculums were changed to 3 mL of DMEM containing 1.5% carboxymethyl cellulose, supplemented with 2% fetal bovine serum and 1% penicillin-streptomycin. The plates were incubated again at 37° C. in a humidified CO2 incubator for 3 days (72±6 hours) until visible plaques formed. At the end of the 3 day incubation period, the overlay was aspirated and U-2 OS cells were stained with 1 mL of 0.1% crystal violet solution for an hour. The number of plaques was counted after removing the crystal violet solution and the titer of each lysate was calculated. The reagents used for the plaque assay are summarized in Table 3.

TABLE 2

Reagents used during JX-594 viral cultures.

| Reagent | Concentration | Source |
|---|---|---|
| JX-594 (PexaVec) | $2.75 \times 10^9$ pfu/ml | Sillajen Lot #: 20140420 |
| Adriamicyn (Doxirubicin hydrochloride) | 10 ug/ml | Sigma |
| Lipiodol Ultra Fluid (Ethyl esters of iodized fatty acids of poppy seed oil) | 2% and 100% | Guerbet, France |
| Gelfoam 150 mm-350 mm (Gelatin Sponge Particle Embolic Agent) | 1 mg/ml | Alicon Pharm SCI & TEC CO., LTD |
| DMEM | NA | Hyclone Cat#SH30243.01 |
| Fetal bovine serum | 2.5% | Hyclone Cat#SH30919.03 |

TABLE 3

Reagents used for viral plaque assays.

| Reagent (for plaque assay) | Final Concentration | Source |
|---|---|---|
| DMEM (liquid) | NA | Hyclone Cat#SH30243.01 |
| DMEM (powder) | 1 X | gibco Cat#12800-017 |
| Fetal bovine serum | 2% | Hyclone Cat#SH30919.03 |
| Carboxymethyl cellulose | 1.5% | Sigma Cat#C-5678 |
| penicillin-streptomycin | 1% | Hyclone Cat#SV30010 |
| Crystal Violet | 0.1% | Sigma Cat#C-6158 |

Results

Figure 1A:
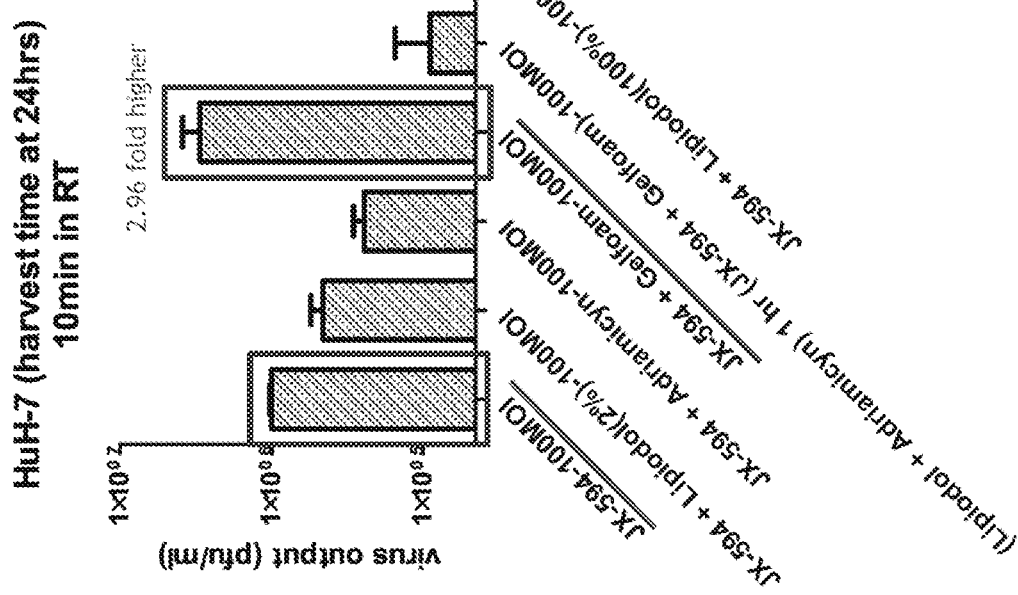
Figure 1C:
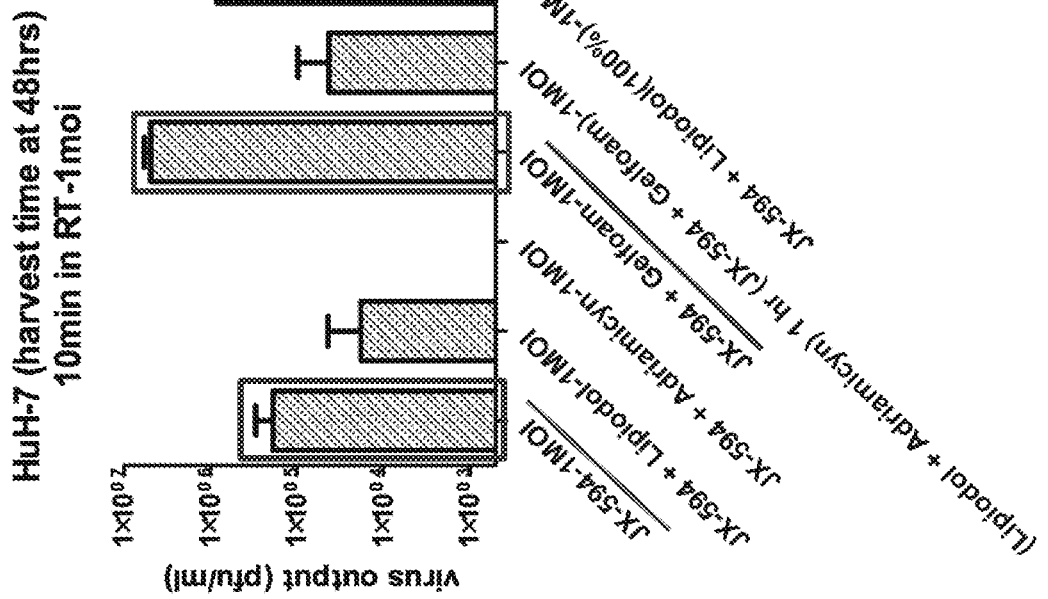
Figure 1D:
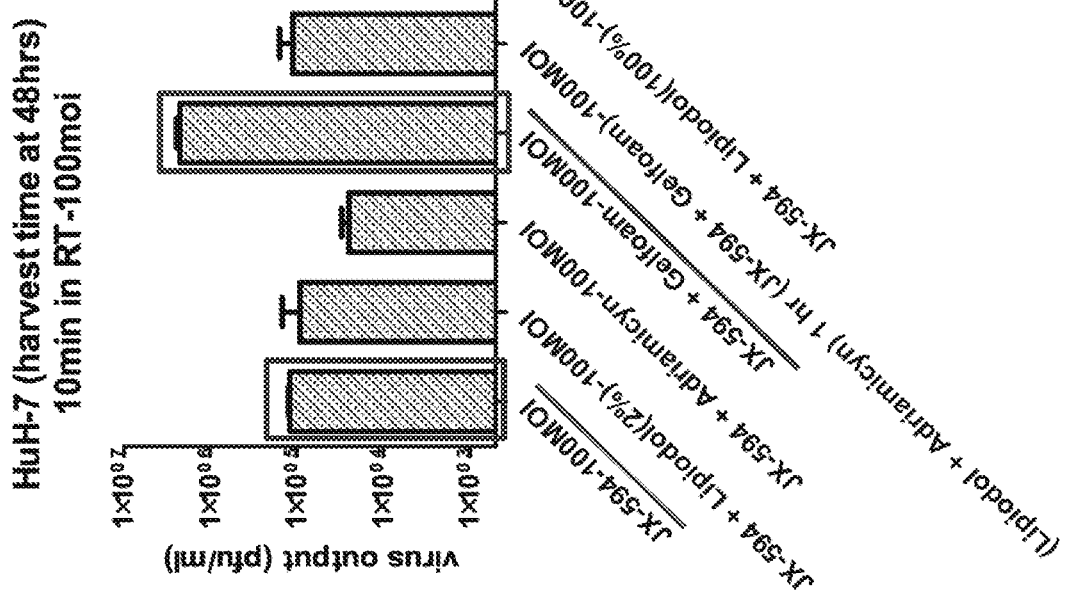

Cellular viral output was increased at 24 and 48 hours when JX-594 virus was incubated with Gelfoam prior to infection (FIGS. 1A-D). Conversely, incubation with Lipiodol and/or Adriamicyn, with and without Gelfoam, decreased viral output at 24 hours (FIGS. 1A&B). At 48 hours, incubation with 2% Lipiodol alone or in combination with Adriamicyn and Gelfoam decreased viral output at a MOI of 1, while incubation with Adriamicyn alone decreased viral output at a MOI of 1 and 100 (FIGS. 1C&D). These results indicate that Gelfoam surprisingly increases JX-594 viral replication by nearly three fold in vitro. Conversely, Adriamicyn and Lipiodol decrease JX-594 viral replication in vitro. Previous studies have shown that addition of embolic agents has no impact on the viral output of smaller viruses with basolateral release such as VSV, as indicated by similar viral growth curves when cultured with and without an embolic agent (Altomonte et al. (2008) *Hepatology* 48:1864-1873). Therefore, the basic embolic agents are compatible with larger oncolytic viruses and/or oncolytic viruses with apical release such as vaccinia viruses and surprisingly even enhance viral output. Without being limited by theory, the increase in viral output may explain why the embolization methods of the disclosure are efficacious even with large oncolytic viruses and viruses that bud from the apical surface such as vaccinia virus.

Example 2: Serum JX-594 Virus Detection

The presence of virus in peripheral blood post embolization of rabbits with Gelfoam formulated JX-594 was evaluated.

Methods

Three normal New Zealand White rabbits (Biogenomics, Seoul, Korea; Samtako, Oh San, South Korea), without VX2 tumor implantation, were embolized with Gelfoam formulated JX-594. Embolotherapy was performed with fluoroscopic guidance. Angiography was usually performed with a transauricular approach, and detailed methods were followed (Chang et al., (2011) *J Vasc Intern Radiol* 22:1181-1187). Right and left central auricular arteries were cannulated to determine which side was advantageous for performing hepatic artery angiography.

For anesthesia, 1.5 mL of a 2:3 mixture of xylazine and tiletamine/zolazepam was injected intramuscularly at the posterior thigh. After anesthesia, the rabbit was placed in the supine position on a fluoroscopic table. Shaving of the hair was unnecessary for transauricular arterial access. The short hair at the puncture site was shaved with an electric clipper. The rabbits' ears were scrubbed with alcohol for sterilization. The central auricular artery was punctured percutaneously in one of the rabbit's ears with an 18-gauge Angiocath needle inserted in the retrograde direction. After advancing the plastic sheath of the Angiocath needle, the inner stylet needle was removed and the hub of the plastic sheath was plugged with the cap of a three-way stopcock. The plastic sheath was fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) were introduced into the central auricular artery by the interventional radiologists. Approximately 1 mL of contrast agent was infused to obtain a roadmap from the extracranial carotid artery to the thoracic aorta. The guide wire was advanced carefully into the descending thoracic aorta, and the proper hepatic artery was then selected by manipulating the guide wire. After placing the tip of the microcatheter in the proper hepatic artery, hepatic artery angiography was performed by hand injection of contrast agent.

A mixture of $1 \times 10^8$ PFU Pexa-Vec (SillaJen, Busan, Korea) and 150 µm-350 µm Gelfoam particles (Alicon, China) was prepared. Half of a vial of Gelfoam was dissolved in 5 mL of contrast media and 5 mL of normal saline, and this mixture was mixed with 1 mL of Pexa-Vec. The end point of embolization was when an occlusion of tumor feeder was achieved. After selection of vessel with microcatheter, embolization was performed using 1.5 mL of prepared mixture of Pexa-Vec and Gelfoam particle. After removing the microcatheter and plastic sheath from the central auricular artery, the puncture site was compressed manually.

A peripheral blood sample was collected at the indicated time points. The blood sample was collected from an ear blood vessel and centrifuged at 3,000 rpm for 5 minutes to separate the serum. DNA in 200 µL of serum was extracted using a QIAamp DNA Blood Mini Kit following the manufacturer's instructions (Blood and Body Fluid Spin Protocol). In short, 20 µL of protease was added in a 1.5 mL microcentrifuge tube and 200 µL of serum was added. 200 µL of lysis buffer AL (QIAGEN, Cat#19075) was added and the tube was incubated at 56° C. for 10 minutes. 200 µL of absolute ethanol was added to the sample and the mixture was transferred to the QIAamp spin column. Once the sample was centrifuged at 6,000×g for 1 minute, the column was washed twice with the provided washing buffers AW1 (QIAGEN, Cat#19081) and AW2 (QIAGEN, Cat#19072). The DNA was eluted in 200 µL of elution buffer AE (QIAGEN, Cat#10977). qPCR analysis was performed on the vaccinia DNA polymerase gene, E9L, using a 7300 Real Time PCR System (Applied Biosystems, model: PRISM7300). qPCR conditions are shown in Table 4. Mean viral quantity was measured. The limit of detection was 5.

TABLE 4

| qPCR conditions | | |
|---|---|---|
| Reagent | Description or Source | Volume for single reaction |
| Primer (F) | 5'-GAA CAT TTT TGG CAG AGA GAG CC-3' (SEQ ID NO: 1) | 1.0 µL |
| Primer (R) | 5'-CAA CTC TTA GCC GAA GCG TAT GAG-3' (SEQ ID NO: 2) | 1.0 µL |

TABLE 4-continued

| qPCR conditions | | |
|---|---|---|
| Probe | 5'FAM-CAG GCT ACC AGT TCA A-MGBNFQ-3' (SEQ ID NO: 3) | 1.0 μL |
| 2X TaqMan Universal PCR Master Mix | Roche, Part#4304437 | 10.0 μL |
| ddH$_2$O | Invitrogen, Cat#10977-015 | 2.0 μL |
| Template | extracted DNA | 5.0 μL |
| Step | Temperature | Time |
| Denaturation | 95° C. | 15 seconds |
| Annealing/ Elongation | 60° C. | 1 minute |

50 cycles, 2 hours and 10 minutes in total

Results

All serum viral detection values (expressed as copy number) were below the limit of detection (Table 5). In table 5, ND refers to a value that was not detected (value=0), while <LOD indicates a value that was below the limit of detection. These results indicate that virus delivered via embolotherapy localizes only to the tumor and does not bleed out of the tumor into other tissues or the bloodstream. Conversely, previous studies have demonstrated that JX-594 virus can be detected within the bloodstream after injection directly into the tumor. In addition, previous studies using VSV virus have demonstrated that VSV is detectable in the bloodstream 1 day after viral embolization, indicating that smaller viruses are not retained well by embolic agents and can therefore reach tissues outside of the tumor (Shinozaki et al. (2004) *Mol Therapy* 9:368-376).

The lack of detectable JX-594 virus delivered via embolotherapy within the systemic circulation is quite surprising. These results indicate that JX-594 embolization represents a safety improvement over direct injection of JX-594 into the tumor or embolization with a smaller virus such as VSV. JX-594 is generally regarded as safe, but other oncolytic viruses could damage or kill healthy tissues elsewhere in the body. JX-594 virus delivered via viral embolotherapy may not be transported outside of the tumor, and therefore is not capable of damaging or killing healthy tissues. Thus, JX-594 viral embolotherapy is a safer alternative to both direct injection into the tumor and viral embolotherapy with a smaller virus such as VSV. Again, without being limited by theory, small viruses such as VSV may not be adequately retained by embolic agents.

TABLE 5

| | Serum virus levels | | | | | | | |
|---|---|---|---|---|---|---|---|---|
| | Before inj. | after inj. | 10 min | 30 min | 1 hr | 4 hr | D1 | D2 |
| Rabbit 1 | <LOD | <LOD | 0 | 0 | 0 | 0 | 0 | 0 |
| Rabbit 2 | 0 | 0 | 0 | 0 | 0 | 0 | 0 | 0 |
| Rabbit 3 | 0 | <LOD | <LOD | 0 | <LOD | 0 | 0 | 0 |

Example 3: Transcatheter Arterial Viroembolization with Pexa-Vec and Gelfoam

The impact of Gelfoam on transcatheter arterial viroembolization with JX-594 oncolytic vaccinia virus (PexaVec) was evaluated in a rabbit VX2 liver tumor model.

Methods

Animal Preparation

Four healthy New Zealand White rabbits (Biogenomics, Seoul, Korea; Samtako, Oh San, South Korea), weighing 2.5-3 kg each, were used in this study.

The VX2 carcinoma strain was maintained by means of successive transplantation into the hindlimb of a carrier rabbit. For anesthesia, 2.5-3 mL of a 2:3 mixture of xylazine (Rompun; Bayer Korea, Seoul, Korea) and tiletamine/zolazepam (Zoletil; Virbac, Carros, France) were injected intramuscularly at the posterior thigh. Through a midline abdominal incision, 0.1 mL of minced VX2 carcinoma (2-3 mm$^3$) was implanted into the subcapsular parenchyma of the left medial lobe of the liver. Fourteen days after tumor implantation, when the tumors were 15-30 mm in diameter, the animals were used for experiments.

One day before PexaVec embolotherapy, computed tomography (CT) was performed (Somatom definition AS; Siemens Medical Systems, Erlangen, Germany) with the animals in prone or decubitus position. Nonenhanced CT was performed to cover the entire liver (1.5-mm collimation, 1.5 pitch, and 1-mm reconstruction interval). For contrast material-enhanced CT, 13 mL of contrast material was injected at a rate of 0.5 mL/sec through the auricular vein. With bolus tracking technique, a hepatic arterial and portal venous phase scan was obtained in 5-second and 16-second intervals (Yoon et al., (2003) *Radiology* 229:126-31).

On the CT scan, the location and size of the tumor were measured. The volume (V) of the tumor was calculated according to the equation $V=L\times S^2/2$, where L is the longest and S is the shortest diameter of the tumor (Okada et al., (1995) *Br J Cancer* 71:518-524; Watanabe et al., (1994) *Oncology* 52:76-81.31).

PexaVec Transcatheter Arterial Viroembolization

Two weeks after implantation of VX2 carcinoma in the liver, Embolotherapy was performed with fluoroscopic guidance. Angiography was usually performed with a transauricular approach, and detailed methods were followed (Chang et al., (2011) *J Vasc Intery Radiol* 22:1181-1187). Right and left central auricular arteries were cannulated to determine which side was advantageous for performing hepatic artery angiography.

For anesthesia, 1.5 mL of a 2:3 mixture of xylazine and tiletamine/zolazepam was injected intramuscularly at the posterior thigh. After anesthesia, the rabbit was placed in the supine position on a fluoroscopic table. Shaving of the hair was unnecessary for transauricular arterial access. The short hair at the puncture site was shaved with an electric clipper. The rabbits' ears were scrubbed with alcohol for sterilization. The central auricular artery was punctured percutaneously in one of the rabbit's ears with an 18-gauge Angiocath needle inserted in the retrograde direction. After advancing the plastic sheath of the Angiocath needle, the inner stylet needle was removed and the hub of the plastic sheath was plugged with the cap of a three-way stopcock. The plastic sheath was fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) were introduced into the central auricular artery by the interventional radiologists. Approximately 1 mL of contrast agent was infused to obtain a roadmap from the extracranial carotid artery to the thoracic aorta. The guide wire was advanced carefully into the descending thoracic aorta, and the proper hepatic artery was then selected by manipulating the guide wire. After placing the tip of the microcatheter in the proper hepatic artery, hepatic artery angiography was performed by hand injection of contrast agent.

A mixture of $1 \times 10^8$ PFU Pexa-Vec (SillaJen, Busan, Korea) and 150 μm-350 μm gelfoam particle (Caligel, Alicon, China) was prepared. Half of a vial of gelfoam was dissolved in 5 cc of contrast media and 5 cc of normal saline, and this mixture was mixed with 1 cc of Pexa-Vec. The end point of embolization was when an occlusion of tumor feeder was achieved. After selection of VX2 tumor with microcatheter, embolization was performed using 1.5 cc of prepared mixture of Pexa-Vec and gelfoam particle. Control animals received embolization with Tris buffer, Pexa-Vec, or Gelfoam alone. After removing the microcatheter and plastic sheath from the central auricular artery, the puncture site was compressed manually. Composition and dosing regimens for the four treatment groups are summarized in Table 6.

TABLE 6

Transcatheter Arterial Viroembolization treatment groups.

| Group # | Treatment | Time of material mixture | Dose | Volume (ul) | Injection route | # of Animals |
|---|---|---|---|---|---|---|
| 1 | 10 mM Tris pH 9 | NA | NA | 100 ul | HAI | 1 |
| 2 | JX-594 | NA | $2 \times 10^8$ pfu | 100 ul | HAI | 1 |
| 3 | Gelfoam + 10 mM Tris pH 9 | 1 h | 2-3 mm3 | 100 ul | HAI | 1 |
| 4 | JX-594 + Gelfoam | 10 min | $2 \times 10^8$ pfu/ 2-3 mm3 | 100 ul | HAI | 1 |

Animal Monitoring

Figures 2A, 2B:
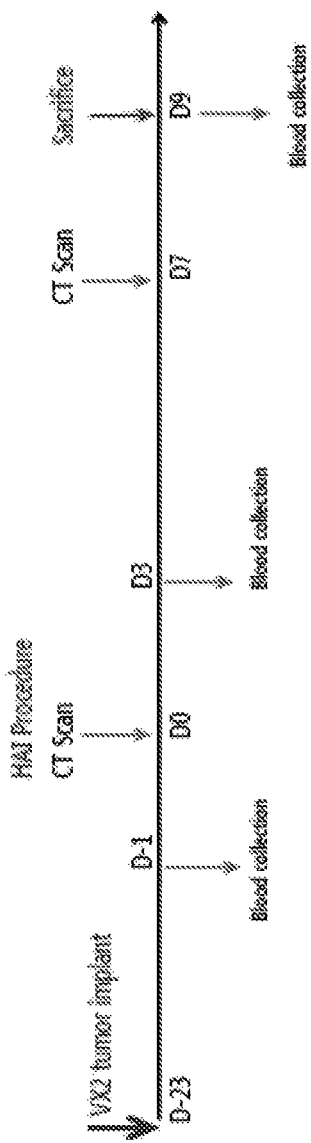
FIG. 2 shows an experimental timeline (FIG. 2A) and tissue collection and analysis plan (FIG. 2B) for transcatheter embolotherapy with Gelfoam formulated Pexa-Vec in a rabbit liver tumor model.

Animals were observed for survival, tumor size, body weight, and appearance according to Table 7. A schematic diagram of the experimental timeline is shown in FIG. 2A. CT scans were performed immediately prior to embolization (day 0) and at day 7. Blood was collected at days −1, 3, and 9. Animals were sacrificed on day 9 (32 days post-tumor implant) and tissues were harvested for analysis (FIG. 2B).

TABLE 7

Animal monitoring schedule

| | |
|---|---|
| Survival | Daily |
| Tumor size | Every other day and just before sacrifice |
| Body weight | Every other day |
| Appearance | Every other day: roughened fur, dehydration, difficulty breathing, lethargy. If found unusual, take photos and report |
| Sacrifice | 32 days post-tumor implant |
| Digital records | ST Scan on procedure day and on day 7 after procedure |

Tissue Imaging

Liver tissue harvested from treated and control animals was stained with hematoxylin and eosin (H&E) to visualize tumors. CT scans were performed with a 128-section CT unit (Somatom Definition AS Plus; Siemens Healthcare) with the following parameters: tube voltages of 120 kVp, effective tube current of 90 mA, field of view of 146 mm, and reconstruction thickness of 2 mm at 2-mm intervals. CT scans at baseline and 23 days after serum treatment initiation were performed on a subset of animals. The CT protocol included the acquisition of non-enhanced images and subsequent acquisition of arterial, venous, and delayed-phase image series after the intravenous bolus injection of 8 to 9 ml of nonionic iodinated contrast material (300 mg of iodine per milliliter of iohexol (Omnipaque; GE Healthcare AS), 2 ml/kg, 2.4 to 2.7 g of iodine) at a rate of 2 ml/s via an ear vein. Arterial phase imaging was obtained 10 s after achieving enhancement of the descending aorta to 100 Hounsfield units, as measured with the bolus tracking technique. Venous phase imaging was obtained 10 s after completion of the arterial phase, and delayed-phase imaging was obtained 70 s after venous phase was complete. To obtain histology samples, VX2 bearing rabbits were euthanized by CO2 inhalation. Subsequently, the abdomen was surgically incised to isolate whole liver tissues which were treated in 10% formalin solution for 2 days. After careful incisions were made to the whole liver crossing the VX2 masses, tissues were embedded in paraffin. After routine H&E staining, histological observation was performed under a ×100-200 light microscope.

Results

An enhanced VX2 tumor mass, with a viable lesion, was observed in CT scans prior to JX-594 embolotherapy (FIG. 3A). Viable VX2 tissue (bright area in FIG. 3A) is surrounded by normal liver parenchyma in histologically stained tissue. VX2 tissue showed 40-50% necrosis without any treatment, indicating spontaneous necrosis of the VX2 mass. The tumor mass was observed in angiography images (black circle) before injection of the JX-594 Gelfoam mixture via the left hepatic artery (FIG. 3C).

However, after arterial injection of the JX-594 Gelfoam mixture, complete tumor necrosis was observed (FIG. 3B and FIG. 3D) both in CT and histology images. The highly necrotic tumor tissue observed after JX-594 embolotherapy is identified in the histological images by the lack of pink tissue staining and absence of visibly stained nuclei (FIG. 3D). These results indicate that a single dose of JX-594 embolotherapy results in complete death of the tumor. Notably, the histology images demonstrate healthy, intact liver tissue outside of the tumor post JX-594 embolotherapy, as indicated by robust pink staining and visibly stained nuclei on the left side of the panel(FIG. 3D) and all of FIG. 3E. This indicates that no damage to normal liver tissue occurs as a result of JX-594 embolotherapy even at the junction between the tumor and healthy tissue as minimum inflammation was observed in the junctional area of the tumor and normal parenchyma (FIG. 3D). These results highlight the exquisite specificity of JX-594 embolotherapy, as the virus exclusively targets the tumor, leading to effective tumor necrosis, without damaging healthy liver tissue.

Therefore, the embolization methods of the present disclosure represent a safe, yet efficacious method to decrease tumoral load.

Without wishing to be bound by theory, it is believed that the Gelfoam embolic agent is effective at holding larger viruses or viruses that are released apically from polarized cells, such as vaccinia viruses, in the proper location during embolotherapy. This sustained localization at the tumor interface in turn contributes to increased delivery and targeted infection of the tumor tissue. Conversely, smaller viruses, such as VSV, are capable of diffusing through embolic agents and dispersing away from the tumor, thereby leading to less targeted delivery and lower infection of tumor tissues. Again, without being limited by theory, increased localization of virus at the target tissue when formulated with Gelfoam may explain why the embolization methods of the disclosure are not just efficacious, but surprisingly effective, even with large oncolytic viruses and viruses that bud from the apical surface such as vaccinia virus.

In addition, these results emphasize the robust efficacy of the embolization methods of the present disclosure, as a single treatment leads to complete tumor necrosis, whereas previously utilized transarterial chemoembolozation methods require repeated treatments to effectively eradicate tumors.

Example 4: Efficacy and PK Modulation of Oncolytic Vaccinia Virus after Transcatheter Arterial Viroembolization in Rabbits The efficacy of transcatheter artertial viroembolization (TAVE) versus oncolytic virotherapy and embolization is evaluated in a rabbit tumor model. Pharmacokinetics (PK) of injected virus is examined by measuring viral particle number in peripheral blood samples.

Methods

Figure 4:
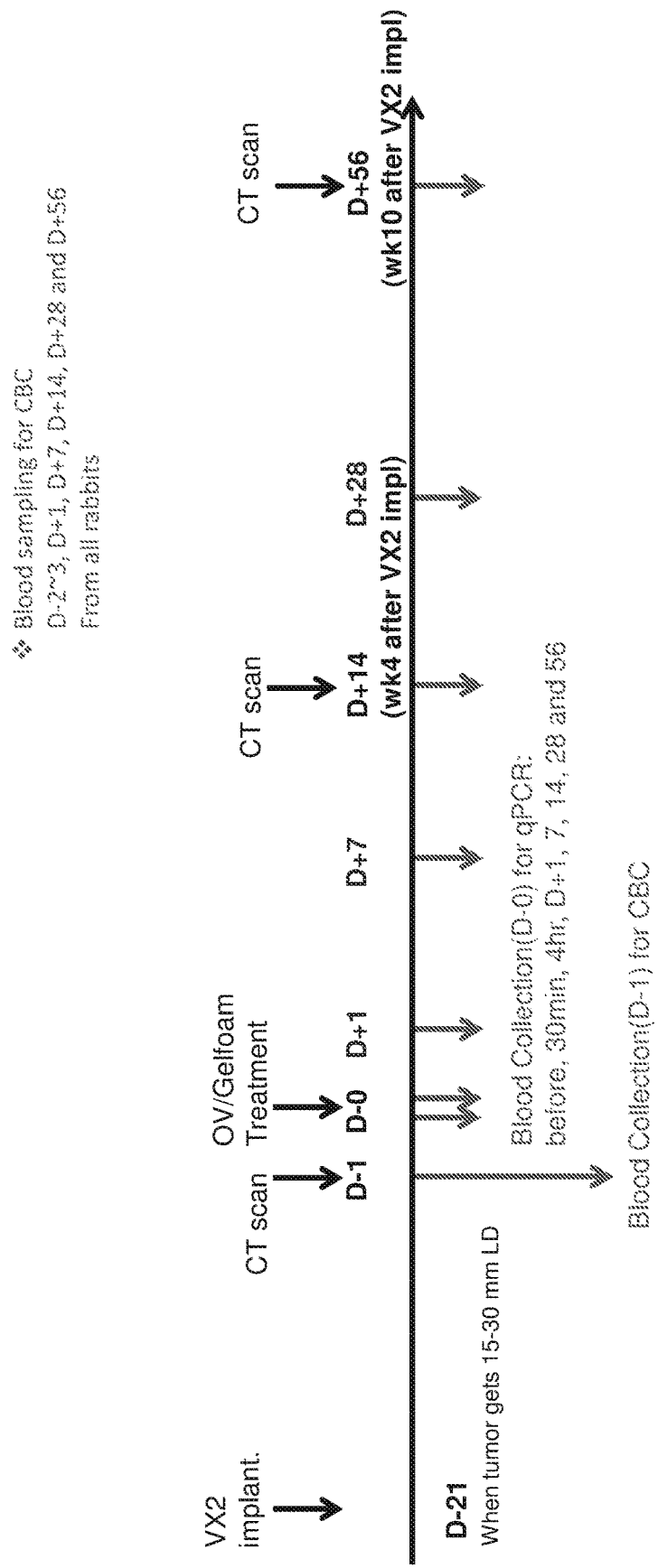
FIG. 4 shows an experimental timeline for efficacy and pharmacokinetic (PK) studies of TAVE versus oncolytic virotherapy and embolization in a rabbit tumor model.

Female New Zealand White rabbits (Biogenomics, Seoul, Korea; Samtako, Oh San, South Korea), weighing 2.5-3 kg each, are used in this study. Anesthesia is performed by injecting 2.5-3.0 mL of a 2:3 mixture of Rompun and Zoletil intramuscularly at the posterior thigh. Minced VX2 carcinoma tumor tissue (0.1 mL) is implanted into the subcapsular parenchyma of the left medial lobe of the liver through a midline abdominal incision, and incubated for 14-23 days until the tumor reaches 15-30 mm in diameter. Vaccinia virus strain vvDD-CDSR, purified by sucrose cushion, is utilized in this study. Embolotherapy is performed according to the methods described in Example 3 using Gelfoam particles (SCION, Alicon, Hangzhou, China), sized 150-350 um. 100 mL of 320 mg/ml Iodixanol (VISIPAQUE, GE Healthcare, Cork, Ireland) is used as a constrast agent during embolization. The treatment groups, dosages, and study design are shown in Table 8 and FIG. 4. The three treatment groups include oncolytic virus (OV) only, transarterial embolization (TAE) only, and transarterial viroembolization (TAVE). Blood is collected 1 day and immediately prior to treatment, and 30 minutes, 4 hours, 1, 7, 14, 28, and 56 days post treatment.

TABLE 8

Study design

| Group | # of rabbit/Gender | Description | Material | Vehicle | Dose, Volume | Injection route |
|---|---|---|---|---|---|---|
| 1 | 3/Female (only 2 for PK) | TAVE | vvDD-CDSR + Gelfoam | Normal saline | 10 mg gelfoam 1 cc saline 1 cc OV 1 cc contrast media | AI |
| 2 | 3/Female (only 2 for PK) | OV only | vvDD-CDSR | Normal saline | 1 × 10$^8$ pfu/ml 1 ml | AI |
| 3 | 3/Female | TAE only | Gelfoam | Normal saline | 50 mg gelfoam 5 cc contrast media 5 cc saline | AI |

Complete blood counts (CBCs) and biochemistry assays are performed on collected blood samples (Table 9). Viral particles in the blood samples are quantified by quantitative-PCR (Q-PCR). Antibody measurements are performed before embolization and at 28 days post treatment using 300 uL of plasma. CT scans are used to measure tumor size before and after embolotherapy. Animal monitoring is performed during the study according to Table 10.

TABLE 9

Volume of blood required for analysis

| Assessment Item | Sample volume required | Whole blood required |
|---|---|---|
| CBC | 1 mL, whole blood | 1 mL |
| Biochemistry | 1 mL, plasma | 2 mL |
| qPCR | 500 uL, serum | 1 mL |

TABLE 10

Animal monitory schedule

| Timeline | Parameter | Note |
|---|---|---|
| Pre-study | Clinical observations | Visual abnormalities |
| In-Life Duration (Every other day) | Clinical observations | Morbidity, Mortality, Clinical signs (fur, dehydration, breathing and etc) Body weight Survival |
| Prior to Sacrifice | Clinical observations | Clinical signs, Body weight |

Example 5: Transcatheter Arterial Viroembolization with vvDD-CDSR Virus and Gelfoam The impact of Gelfoam on transcatheter embolotherapy with vvDD-CDSR oncolytic vaccinia virus is evaluated in a rabbit VX2 liver tumor model.

Methods

Animal Preparation

Four healthy New Zealand White rabbits (Biogenomics, Seoul, Korea; Samtako, Oh San, South Korea), weighing 2.5-3 kg each, are used in this study.

The VX2 carcinoma strain is maintained by means of successive transplantation into the hindlimb of a carrier rabbit. For anesthesia, 2.5-3 mL of a 2:3 mixture of xylazine (Rompun; Bayer Korea, Seoul, Korea) and tiletamine/zolazepam (Zoletil; Virbac, Carros, France) are injected intramuscularly at the posterior thigh. Through a midline abdominal incision, 0.1 mL of minced VX2 carcinoma (2-3 mm$^3$) is implanted into the subcapsular parenchyma of the left medial lobe of the liver. Fourteen days after tumor implantation, when the tumors are 15-30 mm in diameter, the animals are used for experiments.

One day before vvDD-CDSR embolotherapy, computed tomography (CT) is performed (Somatom definition AS; Siemens Medical Systems, Erlangen, Germany) with the animals in prone or decubitus position. Nonenhanced CT is performed to cover the entire liver (1.5-mm collimation, 1.5 pitch, and 1-mm reconstruction interval). For contrast material-enhanced CT, 13 mL of contrast material is injected at a rate of 0.5 mL/sec through the auricular vein. With bolus tracking technique, a hepatic arterial and portal venous phase scan is obtained in 5-second and 16-second intervals (Yoon et al., (2003) *Radiology* 229:126-31).

On the CT scan, the location and size of the tumor is measured. The volume (V) of the tumor is calculated according to the equation $V=L\times S^2/2$, where L is the longest and S is the shortest diameter of the tumor (Okada et al., (1995) *Br J Cancer* 71:518-524; Watanabe et al., (1994) *Oncology* 52:76-81.31).

vvDD-CDSR Transcatheter Arterial Viroembolization

Two weeks after implantation of VX2 carcinoma in the liver, embolotherapy is performed with fluoroscopic guidance. Angiography is usually performed with a transauricular approach, and detailed methods are followed (Chang et al., (2011) *J Vasc Interv Radiol* 22:1181-1187). Right and left central auricular arteries are cannulated to determine which side is advantageous for performing hepatic artery angiography.

For anesthesia, 1.5 mL of a 2:3 mixture of xylazine and tiletamine/zolazepam is injected intramuscularly at the posterior thigh. After anesthesia, the rabbit is placed in the supine position on a fluoroscopic table. Shaving of the hair is unnecessary for transauricular arterial access. The short hair at the puncture site is shaved with an electric clipper. The rabbits' ears are scrubbed with alcohol for sterilization. The central auricular artery is punctured percutaneously in one of the rabbit's ears with an 18-gauge Angiocath needle inserted in the retrograde direction. After advancing the plastic sheath of the Angiocath needle, the inner stylet needle is removed and the hub of the plastic sheath is plugged with the cap of a three-way stopcock. The plastic sheath is fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) are introduced into the central auricular artery by the interventional radiologists. Approximately 1 mL of contrast agent is infused to obtain a roadmap from the extracranial carotid artery to the thoracic aorta. The guide wire is advanced carefully into the descending thoracic aorta, and the proper hepatic artery is then selected by manipulating the guide wire. After placing the tip of the microcatheter in the proper hepatic artery, hepatic artery angiography is performed by hand injection of contrast agent.

A mixture of $1\times10^8$ PFU vvDD-CDSR (Ottawa Hospital Research Institute (OHRI)) and 150 μm-350 μm gelfoam particle (Caligel, Alicon, China) is prepared. One whole vial of gelfoam is dissolved in 10 ml of normal saline with 20 mL syringe and the end of syringe is inserted into one side of the 3-way stopcock. 10 ml of contrast media is prepared in separate 10 mL syringe and inserted in another side of 3-way stopcock. Gel-foam and saline mixture and constrast media are mixed smoothly by pumping plungers. 0.3 ml of gel-foam-saline-contrast media mixture is taken with 1 mL syringe and 1 cc of virus is mixed. The end point of embolization is when an occlusion of tumor feeder is achieved. After selection of VX2 tumor with microcatheter, embolization is performed using 0.4 ml of prepared mixture of virus and gelfoam particle. Control animals receive embolization with Tris buffer, virus, or Gelfoam alone. After removing the microcatheter and plastic sheath from the central auricular artery, the puncture site is compressed manually. Composition and dosing regimens for the four treatment groups are summarized in Table 11.

TABLE 11

Transcatheter Arterial Viroembolization treatment groups.

| Group # | Treatment | Time of material mixture | Dose | Volume (ul) | Injection route | # of Animals |
|---|---|---|---|---|---|---|
| 1 | 10 mM Tris pH 9 | NA | NA | 100 ul | HAI | 1 |
| 2 | vvDD-CDSR | NA | $5 \times 10^7$ pfu | 100 ul | HAI | 1 |
| 3 | Gelfoam + 10 mM Tris pH 9 | 1 h | 2-3 mm3 | 100 ul | HAI | 1 |
| 4 | vvDD-CDSR + Gelfoam | 10 min | $5 \times 10^7$ pfu/ 2-3 mm3 | 100 ul | HAI | 1 |

Animal Monitoring

Animals are observed for survival, tumor size, body weight, and appearance according to Table 12. CT scans are performed immediately prior to embolization (day 0) and at day 7. Blood is collected at days −1, 3, and 9. Animals are sacrificed on day 9 (32 days post-tumor implant) and tissues are harvested for analysis.

TABLE 12

Animal monitoring schedule

| | |
|---|---|
| Survival | Daily |
| Tumor size | Every other day and just before sacrifice |
| Body weight | Every other day |
| Appearance | Every other day: roughened fur, dehydration, difficulty breathing, lethargy. If found unusual, take photos and report |
| Sacrifice | 32 days post-tumor implant |
| Digital records | ST Scan on procedure day and on day 7 after procedure |

Tissue Imaging

Liver tissue harvested from treated and control animals is stained with hematoxylin and eosin (H&E) to visualize tumors. CT scans are performed with a 128-section CT unit (Somatom Definition AS Plus; Siemens Healthcare) with the following parameters: tube voltages of 120 kVp, effective tube current of 90 mA, field of view of 146 mm, and reconstruction thickness of 2 mm at 2-mm intervals. CT scans at baseline and 23 days after serum treatment initiation are performed. The CT protocol includes the acquisition of non-enhanced images and subsequent acquisition of arterial, venous, and delayed-phase image series after the intravenous bolus injection of 8 to 9 ml of nonionic iodinated contrast material (300 mg of iodine per milliliter of iohexol (Omnipaque; GE Healthcare AS), 2 ml/kg, 2.4 to 2.7 g of iodine) at a rate of 2 ml/s via an ear vein. Arterial phase imaging is obtained 10 s after achieving enhancement of the descending aorta to 100 Hounsfield units, as measured with the bolus tracking technique. Venous phase imaging is obtained 10 s after completion of the arterial phase, and delayed-phase imaging is obtained 70 s after venous phase is complete. To obtain histology samples, VX2 bearing rabbits are euthanized by CO2 inhalation. Subsequently, the abdomen is surgically incised to isolate whole liver tissues which are treated in 10% formalin solution for 2 days. After careful incisions are made to the whole liver crossing the VX2 masses, tissues are embedded in paraffin. After routine H&E staining, histological observation is performed under a ×100-200 light microscope.

Example 6: Transcatheter Arterial Viroembolization with SJ-102 Virus and Gelfoam The impact of Gelfoam on transcatheter embolotherapy with SJ-102 oncolytic vaccinia virus is evaluated in a rabbit VX2 liver tumor model.
Methods
Animal Preparation Four healthy New Zealand White rabbits (Biogenomics, Seoul, Korea; Samtako, Oh San, South Korea), weighing 2.5-3 kg each, are used in this study.

The VX2 carcinoma strain is maintained by means of successive transplantation into the hindlimb of a carrier rabbit. For anesthesia, 2.5-3 mL of a 2:3 mixture of xylazine (Rompun; Bayer Korea, Seoul, Korea) and tiletamine/zolazepam (Zoletil; Virbac, Carros, France) are injected intramuscularly at the posterior thigh. Through a midline abdominal incision, 0.1 mL of minced VX2 carcinoma (2-3 mm³) is implanted into the subcapsular parenchyma of the left medial lobe of the liver. Fourteen days after tumor implantation, when the tumors are 15-30 mm in diameter, the animals are used for experiments.

One day before SJ-102 embolotherapy, computed tomography (CT) is performed (Somatom definition AS; Siemens Medical Systems, Erlangen, Germany) with the animals in prone or decubitus position. Nonenhanced CT is performed to cover the entire liver (1.5-mm collimation, 1.5 pitch, and 1-mm reconstruction interval). For contrast material-enhanced CT, 13 mL of contrast material is injected at a rate of 0.5 mL/sec through the auricular vein. With bolus tracking technique, a hepatic arterial and portal venous phase scan is obtained in 5-second and 16-second intervals (Yoon et al., (2003) *Radiology* 229:126-31).

On the CT scan, the location and size of the tumor is measured. The volume (V) of the tumor is calculated according to the equation $V=L \times S^2/2$, where L is the longest and S is the shortest diameter of the tumor (Okada et al., (1995) *Br J Cancer* 71:518-524; Watanabe et al., (1994) *Oncology* 52:76-81.31).
SJ-102 Transcatheter Arterial Viroembolization Two weeks after implantation of VX2 carcinoma in the liver, embolotherapy is performed with fluoroscopic guidance. Angiography is usually performed with a transauricular approach, and detailed methods are followed (Chang et al., (2011) *J Vasc Interv Radiol* 22:1181-1187). Right and left central auricular arteries are cannulated to determine which side is advantageous for performing hepatic artery angiography.

For anesthesia, 1.5 mL of a 2:3 mixture of xylazine and tiletamine/zolazepam is injected intramuscularly at the posterior thigh. After anesthesia, the rabbit is placed in the supine position on a fluoroscopic table. Shaving of the hair is unnecessary for transauricular arterial access. The short hair at the puncture site is shaved with an electric clipper. The rabbits' ears are scrubbed with alcohol for sterilization. The central auricular artery is punctured percutaneously in one of the rabbit's ears with an 18-gauge Angiocath needle inserted in the retrograde direction. After advancing the plastic sheath of the Angiocath needle, the inner stylet needle is removed and the hub of the plastic sheath is plugged with the cap of a three-way stopcock. The plastic sheath is fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) are introduced into the central auricular artery by the interventional radiologists. Approximately 1 mL of contrast agent is infused to obtain a roadmap from the extracranial carotid artery to the thoracic aorta. The guide wire is advanced carefully into the descending thoracic aorta, and the proper hepatic artery is then selected by manipulating the guide wire. After placing the tip of the microcatheter in the proper hepatic artery, hepatic artery angiography is performed by hand injection of contrast agent.

A mixture of $1 \times 10^8$ PFU SJ-102 (generated from Wyeth strain (ATCC)) and 150 μm-350 μm gelfoam particle (Caligel, Alicon, China) is prepared. Half of a vial of gelfoam is dissolved in 5 cc of contrast media and 5 cc of normal saline, and this mixture is mixed with 1 cc of virus. The end point of embolization is when an occlusion of tumor feeder is achieved. After selection of VX2 tumor with microcatheter, embolization is performed using 1.5 cc of prepared mixture of virus and gelfoam particle. Control animals receive embolization with Tris buffer, virus, or Gelfoam alone. After removing the microcatheter and plastic sheath from the central auricular artery, the puncture site is compressed manually. Composition and dosing regimens for the four treatment groups are summarized in Table 13.

TABLE 13

Transcatheter Arterial Viroembolization treatment groups.

| Group # | Treatment | Time of material mixture | Dose | Volume (ul) | Injection route | # of Animals |
|---|---|---|---|---|---|---|
| 1 | 10 mM Tris pH 9 | NA | NA | 100 ul | HAI | 1 |
| 2 | SJ-102 | NA | 5 × 107 pfu | 100 ul | HAI | 1 |
| 3 | Gelfoam + 10 mM Tris pH 9 | 1 h | 2-3 mm3 | 100 ul | HAI | 1 |
| 4 | SJ-102 + Gelfoam | 10 min | 5 × 107 pfu/ 2-3 mm3 | 100 ul | HAI | 1 |

Animal Monitoring

Animals are observed for survival, tumor size, body weight, and appearance according to Table 14. CT scans are performed immediately prior to embolization (day 0) and at day 7. Blood is collected at days −1, 3, and 9. Animals are sacrificed on day 9 (32 days post-tumor implant) and tissues are harvested for analysis.

TABLE 14

Animal monitoring schedule

| | |
|---|---|
| Survival | Daily |
| Tumor size | Every other day and just before sacrifice |
| Body weight | Every other day |
| Appearance | Every other day: roughened fur, dehydration, difficulty breathing, lethargy. If found unusual, take photos and report |
| Sacrifice | 32 days post-tumor implant |
| Digital records | ST Scan on procedure day and on day 7 after procedure |

Tissue Imaging

Liver tissue harvested from treated and control animals is stained with hematoxylin and eosin (H&E) to visualize tumors. CT scans are performed with a 128-section CT unit (Somatom Definition AS Plus; Siemens Healthcare) with the following parameters: tube voltages of 120 kVp, effective tube current of 90 mA, field of view of 146 mm, and reconstruction thickness of 2 mm at 2-mm intervals. CT scans at baseline and 23 days after serum treatment initiation are performed. The CT protocol includes the acquisition of non-enhanced images and subsequent acquisition of arterial, venous, and delayed-phase image series after the intravenous bolus injection of 8 to 9 ml of nonionic iodinated contrast material (300 mg of iodine per milliliter of iohexol (Omnipaque; GE Healthcare AS), 2 ml/kg, 2.4 to 2.7 g of iodine) at a rate of 2 ml/s via an ear vein. Arterial phase imaging is obtained 10 s after achieving enhancement of the descending aorta to 100 Hounsfield units, as measured with the bolus tracking technique. Venous phase imaging is obtained 10 s after completion of the arterial phase, and delayed-phase imaging is obtained 70 s after venous phase is complete. To obtain histology samples, VX2 bearing rabbits are euthanized by CO2 inhalation. Subsequently, the abdomen is surgically incised to isolate whole liver tissues which are treated in 10% formalin solution for 2 days. After careful incisions are made to the whole liver crossing the VX2 masses, tissues are embedded in paraffin. After routine H&E staining, histological observation is performed under a ×100-200 light microscope.

Example 7: Transcatheter Arterial Viroembolization with SJ-103 Virus and Gelfoam The impact of Gelfoam on transcatheter embolotherapy with SJ-103 oncolytic vaccinia virus is evaluated in a rabbit VX2 liver tumor model.

Methods

SJ-103 Virus

SJ-103 attenuated vaccinia virus was engineered from Western Reserve Vaccinia (ATCC VR-1354, TC adapted) by insertion of two selection marker genes into the thymidine kinase (TK) gene of the virus, thereby rendering the TK gene inactive. The gpt selection gene, which confers resistance to an inhibitor of the enzyme inosine monophosphate dehydrogenase, was placed under the control of a p7.5 early-late viral promoter. A GFP fluorescent marker gene was placed under the control of a synthetic early-late promoter. As a result of the TK disruption, the SJ-103 virus selectively targets cancer cells.

Animal Preparation

Four healthy New Zealand White rabbits (Biogenomics, Seoul, Korea; Samtako, Oh San, South Korea), weighing 2.5-3 kg each, are used in this study.

The VX2 carcinoma strain is maintained by means of successive transplantation into the hindlimb of a carrier rabbit. For anesthesia, 2.5-3 mL of a 2:3 mixture of xylazine (Rompun; Bayer Korea, Seoul, Korea) and tiletamine/zolazepam (Zoletil; Virbac, Carros, France) are injected intramuscularly at the posterior thigh. Through a midline abdominal incision, 0.1 mL of minced VX2 carcinoma (2-3 mm$^3$) is implanted into the subcapsular parenchyma of the left medial lobe of the liver. Fourteen days after tumor implantation, when the tumors are 15-30 mm in diameter, the animals are used for experiments.

One day before SJ-103 embolotherapy, computed tomography (CT) is performed (Somatom definition AS; Siemens Medical Systems, Erlangen, Germany) with the animals in prone or decubitus position. Nonenhanced CT is performed to cover the entire liver (1.5-mm collimation, 1.5 pitch, and 1-mm reconstruction interval). For contrast material-enhanced CT, 13 mL of contrast material is injected at a rate of 0.5 mL/sec through the auricular vein. With bolus tracking technique, a hepatic arterial and portal venous phase scan is obtained in 5-second and 16-second intervals (Yoon et al., (2003) *Radiology* 229:126-31).

On the CT scan, the location and size of the tumor is measured. The volume (V) of the tumor is calculated according to the equation $V = L \times S^2/2$, where L is the longest and S is the shortest diameter of the tumor (Okada et al., (1995) *Br J Cancer* 71:518-524; Watanabe et al., (1994) *Oncology* 52:76-81.31).

SJ-103 Transcatheter Arterial Viroembolization

Two weeks after implantation of VX2 carcinoma in the liver, embolotherapy is performed with fluoroscopic guidance. Angiography is usually performed with a transauricular approach, and detailed methods are followed (Chang et al., (2011) *J Vasc Intery Radiol* 22:1181-1187). Right and left central auricular arteries are cannulated to determine which side is advantageous for performing hepatic artery angiography.

For anesthesia, 1.5 mL of a 2:3 mixture of xylazine and tiletamine/zolazepam is injected intramuscularly at the posterior thigh. After anesthesia, the rabbit is placed in the supine position on a fluoroscopic table. Shaving of the hair is unnecessary for transauricular arterial access. The short hair at the puncture site is shaved with an electric clipper. The rabbits' ears are scrubbed with alcohol for sterilization. The central auricular artery is punctured percutaneously in one of the rabbit's ears with an 18-gauge Angiocath needle inserted in the retrograde direction. After advancing the plastic sheath of the Angiocath needle, the inner stylet needle is removed and the hub of the plastic sheath is plugged with the cap of a three-way stopcock. The plastic sheath is fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) are introduced into the central auricular artery by the interventional radiologists. Approximately 1 mL of contrast agent is infused to obtain a roadmap from the extracranial carotid artery to the thoracic aorta. The guide wire is advanced carefully into the descending thoracic aorta, and the proper hepatic artery is then selected by manipulating the guide wire. After placing the tip of the microcatheter in the proper hepatic artery, hepatic artery angiography is performed by hand injection of contrast agent.

A mixture of $1 \times 10^8$ PFU SJ-103 (generated from WR strain (ATCC)) and 150 µm-350 µm gelfoam particle (Caligel, Alicon, China) is prepared. Half of a vial of gelfoam is dissolved in 5 cc of contrast media and 5 cc of normal saline, and this mixture is mixed with 1 cc of virus. The end point of embolization is when an occlusion of tumor feeder is achieved. After selection of VX2 tumor with microcatheter, embolization is performed using 1.5 cc of prepared mixture of virus and gelfoam particle. Control animals receive embolization with Tris buffer, virus, or Gelfoam alone. After removing the microcatheter and plastic sheath from the central auricular artery, the puncture site is compressed manually. Composition and dosing regimens for the four treatment groups are summarized in Table 15.

Animal Monitoring

Animals are observed for survival, tumor size, body weight, and appearance according to Table 16. CT scans are performed immediately prior to embolization (day 0) and at day 7. Blood is collected at days −1, 3, and 9. Animals are sacrificed on day 9 (32 days post-tumor implant) and tissues are harvested for analysis.

TABLE 16

Animal monitoring schedule

| | |
|---|---|
| Survival | Daily |
| Tumor size | Every other day and just before sacrifice |
| Body weight | Every other day |
| Appearance | Every other day: roughened fur, dehydration, difficulty breathing, lethargy. If found unusual, take photos and report |
| Sacrifice | 32 days post-tumor implant |
| Digital records | ST Scan on procedure day and on day 7 after procedure |

Tissue Imaging

Liver tissue harvested from treated and control animals is stained with hematoxylin and eosin (H&E) to visualize tumors. CT scans are performed with a 128-section CT unit (Somatom Definition AS Plus; Siemens Healthcare) with the following parameters: tube voltages of 120 kVp, effective tube current of 90 mA, field of view of 146 mm, and reconstruction thickness of 2 mm at 2-mm intervals. CT scans at baseline and 23 days after serum treatment initiation are performed. The CT protocol includes the acquisition of non-enhanced images and subsequent acquisition of arterial, venous, and delayed-phase image series after the intravenous bolus injection of 8 to 9 ml of nonionic iodinated con-trast material (300 mg of iodine per milliliter of iohexol (Omnipaque; GE Healthcare AS), 2 ml/kg, 2.4 to 2.7 g of iodine) at a rate of 2 ml/s via an ear vein. Arterial phase imaging is obtained 10 s after achieving enhancement of the descending aorta to 100 Hounsfield units, as measured with the bolus tracking technique. Venous phase imaging is obtained 10 s after completion of the arterial phase, and delayed-phase imaging is obtained 70 s after venous phase is complete. To obtain histology samples, VX2 bearing rabbits are euthanized by CO2 inhalation. Subsequently, the abdomen is surgically incised to isolate whole liver tissues which are treated in 10% formalin solution for 2 days. After careful incisions are made to the whole liver crossing the VX2 masses, tissues are embedded in paraffin. After routine H&E staining, histological observation is performed under a ×100-200 light microscope.

TABLE 15

Transcatheter Arterial Viroembolization treatment groups.

| Group # | Treatment | Time of material mixture | Dose | Volume (ul) | Injection route | # of Animals |
|---|---|---|---|---|---|---|
| 1 | 10 mM Tris pH 9 | NA | NA | 100 ul | HAI | 1 |
| 2 | SJ-103 | NA | 5 × 107 pfu | 100 ul | HAI | 1 |
| 3 | Gelfoam + 10 mM Tris pH 9 | 1 h | 2-3 mm3 | 100 ul | HAI | 1 |
| 4 | SJ-103 + Gelfoam | 10 min | 5 × 107 pfu/ 2-3 mm3 | 100 ul | HAI | 1 |

Example 8: Transcatheter Arterial Viroembolization with WR-TK(−) Virus and Gelfoam The impact of Gelfoam on transcatheter embolotherapy with WR-TK(−) oncolytic vaccinia virus is evaluated in a rabbit VX2 liver tumor model.

Methods

Animal Preparation

Four healthy New Zealand White rabbits (Biogenomics, Seoul, Korea; Samtako, Oh San, South Korea), weighing 2.5-3 kg each, are used in this study.

The VX2 carcinoma strain is maintained by means of successive transplantation into the hindlimb of a carrier rabbit. For anesthesia, 2.5-3 mL of a 2:3 mixture of xylazine (Rompun; Bayer Korea, Seoul, Korea) and tiletamine/zolazepam (Zoletil; Virbac, Carros, France) are injected intramuscularly at the posterior thigh. Through a midline abdominal incision, 0.1 mL of minced VX2 carcinoma (2-3 mm$^3$) is implanted into the subcapsular parenchyma of the left medial lobe of the liver. Fourteen days after tumor implantation, when the tumors are 15-30 mm in diameter, the animals are used for experiments.

One day before WR-TK(−) embolotherapy, computed tomography (CT) is performed (Somatom definition AS; Siemens Medical Systems, Erlangen, Germany) with the animals in prone or decubitus position. Nonenhanced CT is performed to cover the entire liver (1.5-mm collimation, 1.5 pitch, and 1-mm reconstruction interval). For contrast material-enhanced CT, 13 mL of contrast material is injected at a rate of 0.5 mL/sec through the auricular vein. With bolus tracking technique, a hepatic arterial and portal venous phase scan is obtained in 5-second and 16-second intervals (Yoon et al., (2003) *Radiology* 229:126-31).

On the CT scan, the location and size of the tumor is measured. The volume (V) of the tumor is calculated according to the equation $V = L \times S^2 / 2$, where L is the longest and S is the shortest diameter of the tumor (Okada et al., (1995) *Br J Cancer* 71:518-524; Watanabe et al., (1994) *Oncology* 52:76-81.31).

WR-TK(−)Transcatheter Arterial Viroembolization

Two weeks after implantation of VX2 carcinoma in the liver, embolotherapy is performed with fluoroscopic guidance. Angiography is usually performed with a transauricular approach, and detailed methods are followed (Chang et al., (2011) *J Vasc Interv Radiol* 22:1181-1187). Right and left central auricular arteries are cannulated to determine which side is advantageous for performing hepatic artery angiography.

For anesthesia, 1.5 mL of a 2:3 mixture of xylazine and tiletamine/zolazepam is injected intramuscularly at the posterior thigh. After anesthesia, the rabbit is placed in the supine position on a fluoroscopic table. Shaving of the hair is unnecessary for transauricular arterial access. The short hair at the puncture site is shaved with an electric clipper. The rabbits' ears are scrubbed with alcohol for sterilization. The central auricular artery is punctured percutaneously in one of the rabbit's ears with an 18-gauge Angiocath needle inserted in the retrograde direction. After advancing the plastic sheath of the Angiocath needle, the inner stylet needle is removed and the hub of the plastic sheath is plugged with the cap of a three-way stopcock. The plastic sheath is fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) are introduced into the central auricular artery by the interventional radiologists. Approximately 1 mL of contrast agent is infused to obtain a roadmap from the extracranial carotid artery to the thoracic aorta. The guide wire is advanced carefully into the descending thoracic aorta, and the proper hepatic artery is then selected by manipulating the guide wire. After placing the tip of the microcatheter in the proper hepatic artery, hepatic artery angiography is performed by hand injection of contrast agent.

A mixture of $1 \times 10^8$ PFU WR-TK(−) and 150 μm-350 μm gelfoam particle (Caligel, Alicon, China) is prepared. Half of a vial of gelfoam is dissolved in 5 cc of contrast media and 5 cc of normal saline, and this mixture is mixed with 1 cc of virus. The end point of embolization is when an occlusion of tumor feeder is achieved. After selection of VX2 tumor with microcatheter, embolization is performed using 1.5 cc of prepared mixture of virus and gelfoam particle. Control animals receive embolization with Tris buffer, virus, or Gelfoam alone. After removing the microcatheter and plastic sheath from the central auricular artery, the puncture site is compressed manually. Composition and dosing regimens for the four treatment groups are summarized in Table 17.

TABLE 17

Transcatheter Arterial Viroembolization treatment groups.

| Group # | Treatment | Time of material mixture | Dose | Volume (ul) | Injection route | # of Animals |
|---|---|---|---|---|---|---|
| 1 | 10 mM Tris pH 9 | NA | NA | 100 ul | HAI | 1 |
| 2 | WR-TK(−) | NA | 5 × 107 pfu | 100 ul | HAI | 1 |
| 3 | Gelfoam + 10 mM Tris pH 9 | 1 h | 2-3 mm3 | 100 ul | HAI | 1 |
| 4 | WR-TK(−) + Gelfoam | 10 min | 5 × 107 pfu/ 2-3 mm3 | 100 ul | HAI | 1 |

Animal Monitoring

Animals are observed for survival, tumor size, body weight, and appearance according to Table 18. CT scans are performed immediately prior to embolization (day 0) and at day 7. Blood is collected at days −1, 3, and 9. Animals are sacrificed on day 9 (32 days post-tumor implant) and tissues are harvested for analysis.

TABLE 18

Animal monitoring schedule

| | |
|---|---|
| Survival | Daily |
| Tumor size | Every other day and just before sacrifice |
| Body weight | Every other day |

TABLE 18-continued

Animal monitoring schedule

| | |
|---|---|
| Survival | Daily |
| Appearance | Every other day: roughened fur, dehydration, difficulty breathing, lethargy. If found unusual, take photos and report |
| Sacrifice | 32 days post-tumor implant |
| Digital records | ST Scan on procedure day and on day 7 after procedure |

Tissue Imaging

Liver tissue harvested from treated and control animals is stained with hematoxylin and eosin (H&E) to visualize tumors. CT scans are performed with a 128-section CT unit (Somatom Definition AS Plus; Siemens Healthcare) with the following parameters: tube voltages of 120 kVp, effective tube current of 90 mA, field of view of 146 mm, and reconstruction thickness of 2 mm at 2-mm intervals. CT scans at baseline and 23 days after serum treatment initiation are performed. The CT protocol includes the acquisition of non-enhanced images and subsequent acquisition of arterial, venous, and delayed-phase image series after the intravenous bolus injection of 8 to 9 ml of nonionic iodinated con-trast material (300 mg of iodine per milliliter of iohexol (Omnipaque; GE Healthcare AS), 2 ml/kg, 2.4 to 2.7 g of iodine) at a rate of 2 ml/s via an ear vein. Arterial phase imaging is obtained 10 s after achieving enhancement of the descending aorta to 100 Hounsfield units, as measured with the bolus tracking technique. Venous phase imaging is obtained 10 s after completion of the arterial phase, and delayed-phase imaging is obtained 70 s after venous phase is complete. To obtain histology samples, VX2 bearing rabbits are euthanized by CO2 inhalation. Subsequently, the abdomen is surgically incised to isolate whole liver tissues which are treated in 10% formalin solution for 2 days. After careful incisions are made to the whole liver crossing the VX2 masses, tissues are embedded in paraffin. After routine H&E staining, histological observation is performed under a ×100-200 light microscope.

Example 9: Transcatheter Arterial Viroembolization with vvDD Virus and Gelfoam

The impact of Gelfoam on transcatheter embolotherapy with vvDD oncolytic vaccinia virus is evaluated in a rabbit VX2 liver tumor model.
Methods
Animal Preparation Four healthy New Zealand White rabbits (Biogenomics, Seoul, Korea; Samtako, Oh San, South Korea), weighing 2.5-3 kg each, are used in this study.

The VX2 carcinoma strain is maintained by means of successive transplantation into the hindlimb of a carrier rabbit. For anesthesia, 2.5-3 mL of a 2:3 mixture of xylazine (Rompun; Bayer Korea, Seoul, Korea) and tiletamine/zolazepam (Zoletil; Virbac, Carros, France) are injected intramuscularly at the posterior thigh. Through a midline abdominal incision, 0.1 mL of minced VX2 carcinoma (2-3 mm$^3$) is implanted into the subcapsular parenchyma of the left medial lobe of the liver. Fourteen days after tumor implantation, when the tumors are 15-30 mm in diameter, the animals are used for experiments.

One day before vvDD embolotherapy, computed tomography (CT) is performed (Somatom definition AS; Siemens Medical Systems, Erlangen, Germany) with the animals in prone or decubitus position. Nonenhanced CT is performed to cover the entire liver (1.5-mm collimation, 1.5 pitch, and 1-mm reconstruction interval). For contrast material-enhanced CT, 13 mL of contrast material is injected at a rate of 0.5 mL/sec through the auricular vein. With bolus tracking technique, a hepatic arterial and portal venous phase scan is obtained in 5-second and 16-second intervals (Yoon et al., (2003) *Radiology* 229:126-31).

On the CT scan, the location and size of the tumor is measured. The volume (V) of the tumor is calculated according to the equation $V=L \times S^2/2$, where L is the longest and S is the shortest diameter of the tumor (Okada et al., (1995) *Br J Cancer* 71:518-524; Watanabe et al., (1994) *Oncology* 52:76-81.31).

vvDD Transcatheter Arterial Viroembolization

Two weeks after implantation of VX2 carcinoma in the liver, embolotherapy is performed with fluoroscopic guidance. Angiography is usually performed with a transauricular approach, and detailed methods are followed (Chang et al., (2011) *J Vasc Interv Radiol* 22:1181-1187). Right and left central auricular arteries are cannulated to determine which side is advantageous for performing hepatic artery angiography.

For anesthesia, 1.5 mL of a 2:3 mixture of xylazine and tiletamine/zolazepam is injected intramuscularly at the posterior thigh. After anesthesia, the rabbit is placed in the supine position on a fluoroscopic table. Shaving of the hair is unnecessary for transauricular arterial access. The short hair at the puncture site is shaved with an electric clipper. The rabbits' ears are scrubbed with alcohol for sterilization. The central auricular artery is punctured percutaneously in one of the rabbit's ears with an 18-gauge Angiocath needle inserted in the retrograde direction. After advancing the plastic sheath of the Angiocath needle, the inner stylet needle is removed and the hub of the plastic sheath is plugged with the cap of a three-way stopcock. The plastic sheath is fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) are introduced into the central auricular artery by the interventional radiologists. Approximately 1 mL of contrast agent is infused to obtain a roadmap from the extracranial carotid artery to the thoracic aorta. The guide wire is advanced carefully into the descending thoracic aorta, and the proper hepatic artery is then selected by manipulating the guide wire. After placing the tip of the microcatheter in the proper hepatic artery, hepatic artery angiography is performed by hand injection of contrast agent.

A mixture of $1 \times 10^8$ PFU vvDD (OHRI) and 150 µm-350 µm gelfoam particle (Caligel, Alicon, China) is prepared. Half of a vial of gelfoam is dissolved in 5 cc of contrast media and 5 cc of normal saline, and this mixture is mixed with 1 cc of virus. The end point of embolization is when an occlusion of tumor feeder is achieved. After selection of VX2 tumor with microcatheter, embolization is performed using 1.5 cc of prepared mixture of virus and gelfoam particle. Control animals receive embolization with Tris buffer, virus, or Gelfoam alone. After removing the microcatheter and plastic sheath from the central auricular artery, the puncture site is compressed manually. Composition and dosing regimens for the four treatment groups are summarized in Table 19.

TABLE 19

Transcatheter Arterial Viroembolization treatment groups.

| Group # | Treatment | Time of material mixture | Dose | Volume (ul) | Injection route | # of Animals |
|---|---|---|---|---|---|---|
| 1 | 10 mM Tris pH 9 | NA | NA | 100 ul | HAI | 1 |
| 2 | vvDD | NA | 5 × 107 pfu | 100 ul | HAI | 1 |
| 3 | Gelfoam + 10 mM Tris pH 9 | 1 h | 2-3 mm3 | 100 ul | HAI | 1 |
| 4 | vvDD + Gelfoam | 10 min | 5 × 107 pfu/ 2-3 mm3 | 100 ul | HAI | 1 |

Animal Monitoring

Animals are observed for survival, tumor size, body weight, and appearance according to Table 20. CT scans are performed immediately prior to embolization (day 0) and at day 7. Blood is collected at days −1, 3, and 9. Animals are sacrificed on day 9 (32 days post-tumor implant) and tissues are harvested for analysis.

TABLE 20

Animal monitoring schedule

| | |
|---|---|
| Survival | Daily |
| Tumor size | Every other day and just before sacrifice |
| Body weight | Every other day |
| Appearance | Every other day: roughened fur, dehydration, difficulty breathing, lethargy. If found unusual, take photos and report |
| Sacrifice | 32 days post-tumor implant |
| Digital records | ST Scan on procedure day and on day 7 after procedure |

Tissue Imaging

Liver tissue harvested from treated and control animals is stained with hematoxylin and eosin (H&E) to visualize tumors. CT scans are performed with a 128-section CT unit (Somatom Definition AS Plus; Siemens Healthcare) with the following parameters: tube voltages of 120 kVp, effective tube current of 90 mA, field of view of 146 mm, and reconstruction thickness of 2 mm at 2-mm intervals. CT scans at baseline and 23 days after serum treatment initiation are performed. The CT protocol includes the acquisition of non-enhanced images and subsequent acquisition of arterial, venous, and delayed-phase image series after the intravenous bolus injection of 8 to 9 ml of nonionic iodinated contrast material (300 mg of iodine per milliliter of iohexol (Omnipaque; GE Healthcare AS), 2 ml/kg, 2.4 to 2.7 g of iodine) at a rate of 2 ml/s via an ear vein. Arterial phase imaging is obtained 10 s after achieving enhancement of the descending aorta to 100 Hounsfield units, as measured with the bolus tracking technique. Venous phase imaging is obtained 10 s after completion of the arterial phase, and delayed-phase imaging is obtained 70 s after venous phase is complete. To obtain histology samples, VX2 bearing rabbits are euthanized by CO2 inhalation. Subsequently, the abdomen is surgically incised to isolate whole liver tissues which are treated in 10% formalin solution for 2 days. After careful incisions are made to the whole liver crossing the VX2 masses, tissues are embedded in paraffin. After routine H&E staining, histological observation is performed under a ×100-200 light microscope.

Example 10: Transcatheter Arterial Viroembolization with HSV-1 and Gelfoam

The impact of Gelfoam on transcatheter embolotherapy with HSV-1 is evaluated in a rabbit VX2 liver tumor model.
Methods
Animal Preparation Four healthy New Zealand White rabbits (Biogenomics, Seoul, Korea; Samtako, Oh San, South Korea), weighing 2.5-3 kg each, are used in this study.

The VX2 carcinoma strain is maintained by means of successive transplantation into the hindlimb of a carrier rabbit. For anesthesia, 2.5-3 mL of a 2:3 mixture of xylazine (Rompun; Bayer Korea, Seoul, Korea) and tiletamine/zolazepam (Zoletil; Virbac, Carros, France) are injected intramuscularly at the posterior thigh. Through a midline abdominal incision, 0.1 mL of minced VX2 carcinoma (2-3 mm$^3$) is implanted into the subcapsular parenchyma of the left medial lobe of the liver. Fourteen days after tumor implantation, when the tumors are 15-30 mm in diameter, the animals are used for experiments.

One day before HSV-1 embolotherapy, computed tomography (CT) is performed (Somatom definition AS; Siemens Medical Systems, Erlangen, Germany) with the animals in prone or decubitus position. Nonenhanced CT is performed to cover the entire liver (1.5-mm collimation, 1.5 pitch, and 1-mm reconstruction interval). For contrast material-enhanced CT, 13 mL of contrast material is injected at a rate of 0.5 mL/sec through the auricular vein. With bolus tracking technique, a hepatic arterial and portal venous phase scan is obtained in 5-second and 16-second intervals (Yoon et al., (2003) *Radiology* 229:126-31).

On the CT scan, the location and size of the tumor is measured. The volume (V) of the tumor is calculated according to the equation $V = L \times S^2/2$, where L is the longest and S is the shortest diameter of the tumor (Okada et al., (1995) *Br J Cancer* 71:518-524; Watanabe et al., (1994) *Oncology* 52:76-81.31).

HSV-1 Transcatheter Arterial Viroembolization

Two weeks after implantation of VX2 carcinoma in the liver, embolotherapy is performed with fluoroscopic guidance. Angiography is usually performed with a transauricular approach, and detailed methods are followed (Chang et al., (2011) *J Vasc Interv Radiol* 22:1181-1187). Right and left central auricular arteries are cannulated to determine which side is advantageous for performing hepatic artery angiography.

For anesthesia, 1.5 mL of a 2:3 mixture of xylazine and tiletamine/zolazepam is injected intramuscularly at the posterior thigh. After anesthesia, the rabbit is placed in the supine position on a fluoroscopic table. Shaving of the hair is unnecessary for transauricular arterial access. The short hair at the puncture site is shaved with an electric clipper. The rabbits' ears are scrubbed with alcohol for sterilization. The central auricular artery is punctured percutaneously in one of the rabbit's ears with an 18-gauge Angiocath needle inserted in the retrograde direction. After advancing the plastic sheath of the Angiocath needle, the inner stylet needle is removed and the hub of the plastic sheath is plugged with the cap of a three-way stopcock. The plastic sheath is fixed by applying sticking plaster.

After applying a modified drilled cap to the hub of plastic sheath, a 2.0-F microcatheter (Progreat, Terumo, Tokyo, Japan) and a 0.016-inch guide wire (Meister, Asahi intec, Aichi, Co, Ltd, Japan) are introduced into the central auricular artery by the interventional radiologists. Approximately 1 mL of contrast agent is infused to obtain a roadmap from the extracranial carotid artery to the thoracic aorta. The guide wire is advanced carefully into the descending thoracic aorta, and the proper hepatic artery is then selected by manipulating the guide wire. After placing the tip of the microcatheter in the proper hepatic artery, hepatic artery angiography is performed by hand injection of contrast agent.

A mixture of $1 \times 10^8$ PFU HSV-1 and 150 μm-350 μm gelfoam particle (Caligel, Alicon, China) is prepared. Half of a vial of gelfoam is dissolved in 5 cc of contrast media and 5 cc of normal saline, and this mixture is mixed with 1 cc of virus. The end point of embolization is when an occlusion of tumor feeder is achieved. After selection of VX2 tumor with microcatheter, embolization is performed using 1.5 cc of prepared mixture of virus and gelfoam particle. Control animals receive embolization with Tris buffer, virus, or Gelfoam alone. After removing the microcatheter and plastic sheath from the central auricular artery, the puncture site is compressed manually. Composition and dosing regimens for the four treatment groups are summarized in Table 21.

TABLE 21

Transcatheter Arterial Viroembolization treatment groups.

| Group # | Treatment | Time of material mixture | Dose | Volume (ul) | Injection route | # of Animals |
|---|---|---|---|---|---|---|
| 1 | 10 mM Tris pH 9 | NA | NA | 100 ul | HAI | 1 |
| 2 | HSV-1 | NA | $5 \times 10^7$ pfu | 100 ul | HAI | 1 |
| 3 | Gelfoam + 10 mM Tris pH 9 | 1 h | 2-3 mm3 | 100 ul | HAI | 1 |
| 4 | HSV-1 + Gelfoam | 10 min | $5 \times 10^7$ pfu/ 2-3 mm3 | 100 ul | HAI | 1 |

Animal Monitoring

Animals are observed for survival, tumor size, body weight, and appearance according to Table 26. CT scans are performed immediately prior to embolization (day 0) and at day 7. Blood is collected at days −1, 3, and 9. Animals are sacrificed on day 9 (32 days post-tumor implant) and tissues are harvested for analysis.

TABLE 22

Animal monitoring schedule

| | |
|---|---|
| Survival | Daily |
| Tumor size | Every other day and just before sacrifice |
| Body weight | Every other day |

TABLE 22-continued

Animal monitoring schedule

| | |
|---|---|
| Survival | Daily |
| Appearance | Every other day: roughened fur, dehydration, difficulty breathing, lethargy. If found unusual, take photos and report |
| Sacrifice | 32 days post-tumor implant |
| Digital records | ST Scan on procedure day and on day 7 after procedure |

Tissue Imaging

Liver tissue harvested from treated and control animals is stained with hematoxylin and eosin (H&E) to visualize tumors. CT scans are performed with a 128-section CT unit (Somatom Definition AS Plus; Siemens Healthcare) with the following parameters: tube voltages of 120 kVp, effective tube current of 90 mA, field of view of 146 mm, and reconstruction thickness of 2 mm at 2-mm intervals. CT scans at baseline and 23 days after serum treatment initiation are performed. The CT protocol includes the acquisition of non-enhanced images and subsequent acquisition of arterial, venous, and delayed-phase image series after the intravenous bolus injection of 8 to 9 ml of nonionic iodinated contrast material (300 mg of iodine per milliliter of iohexol (Omnipaque; GE Healthcare AS), 2 ml/kg, 2.4 to 2.7 g of iodine) at a rate of 2 ml/s via an ear vein. Arterial phase imaging is obtained 10 s after achieving enhancement of the descending aorta to 100 Hounsfield units, as measured with the bolus tracking technique. Venous phase imaging is obtained 10 s after completion of the arterial phase, and delayed-phase imaging is obtained 70 s after venous phase is complete. To obtain histology samples, VX2 bearing rabbits are euthanized by CO2 inhalation. Subsequently, the abdomen is surgically incised to isolate whole liver tissues which are treated in 10% formalin solution for 2 days. After careful incisions are made to the whole liver crossing the VX2 masses, tissues are embedded in paraffin. After routine H&E staining, histological observation is performed under a ×100-200 light microscope. This example demonstrates that oncolytic HSV-1 virus (including, without limitation, a JS-1 strains of HIV-1 modified by inactivation of the ICP34.5 and ICP47 genes and addition of the human GM-CSF gene) may be used to treat liver cancers via the emolization methods for the present application (including, for example, melanoma cancers that have metastatasized to the liver).

The invention claimed is:

1. A composition comprising an oncolytic vaccinia virus or an oncolytic Herpes simplex virus type 1 (HSV-1) and an agent for active embolization, wherein the active embolization agent is selected from degradable starch, polyvinyl alcohol, gelatin foam, and sulfonated polyvinyl alcohol hydrogel.

2. The composition of claim 1, wherein the oncolytic vaccinia virus does not comprise an active thymidine kinase gene.

3. The composition of claim 1, wherein the oncolytic vaccinia virus does not comprise an active vaccinia growth factor (VGF) gene.

4. The composition of claim 1, wherein the oncolytic vaccinia virus further comprises one or more of a granulocyte-macrophage colony stimulating factor protein, a cytosine deaminase protein, and a somatostatin receptor type 2 protein.

5. The composition of claim 1, wherein the active embolization agent comprises microparticles that are between 100 μm and 2000 μm in diameter.

6. The composition of claim 1, wherein the active embolization agent comprises particulates that are between 10 and 200 μm in diameter.

7. The composition of claim 1, wherein the active embolization agent is a temporary embolic agent or a permanent embolic agent.

8. A method for active embolization of a vascular site in a mammal, comprising introducing into the vasculature of a mammal the composition of claim 1.

9. The method of claim 8, wherein the vascular site is a tumor, supplies blood to the tumor, or is proximal to the tumor.

10. The method of claim 9, wherein the tumor is in the liver.

11. The method of claim 9, wherein the tumor is a primary tumor or a secondary tumor.

12. The method of claim 11, wherein the secondary tumor is a metastasized malignant melanoma.

13. The method of claim 8, wherein the mammal is a human.

14. A method for treating cancer by debulking a hepatic tumor mass, comprising applying the method of claim 8, wherein the method induces necrosis in at least 75% of the embolized tumor mass, and wherein the composition is introduced into the hepatic artery.

15. The method of claim 14, wherein the method induces necrosis in at least 80% of the embolized tumor mass.

16. The method of claim 1, wherein the composition comprises gelatin foam.

17. The method of claim 14, wherein the composition comprises gelatin foam.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct

<400> SEQUENCE: 1
gaacattttt ggcagagaga gcc                                              23

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
caactcttag ccgaagcgta tgag                                             24

<210> SEQ ID NO 3
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: FAM modification
<220> FEATURE:
<221> NAME/KEY: misc_feature
<222> LOCATION: 16
<223> OTHER INFORMATION: MGBNFQ modification

<400> SEQUENCE: 3
caggctacca gttcaa                                                      16
```